(12) United States Patent
Ghosh et al.

(10) Patent No.: US 10,940,321 B2
(45) Date of Patent: Mar. 9, 2021

(54) SYSTEMS, METHODS, AND INTERFACES FOR USE IN CARDIAC EVALUATION

(71) Applicant: Medtronic, Inc., Minneapolis, MN (US)

(72) Inventors: Subham Ghosh, Blaine, MN (US); Karen Kleckner, Blaine, MN (US); Melissa Rhodes, Columbia Heights, MN (US); D'Anne Kudlik, Lino Lakes, MN (US); Jordyn Reich, Minneapolis, MN (US); Keelia Doyle, Minneapolis, MN (US); Joshua Blauer, White Bear Lake, MN (US)

(73) Assignee: Medtronic, Inc., Minneapolis, MN (US)

(*) Notice: Subject to any disclaimer, the term of this patent is extended or adjusted under 35 U.S.C. 154(b) by 207 days.

(21) Appl. No.: 15/995,406

(22) Filed: Jun. 1, 2018

(65) Prior Publication Data
US 2019/0366106 A1   Dec. 5, 2019

(51) Int. Cl.
*A61N 1/372* (2006.01)
*A61B 34/20* (2016.01)
(Continued)

(52) U.S. Cl.
CPC ........ *A61N 1/37247* (2013.01); *A61B 5/0006* (2013.01); *A61B 5/044* (2013.01); *A61B 5/0452* (2013.01); *A61B 5/04085* (2013.01); *A61B 5/6823* (2013.01); *A61B 5/6843* (2013.01); *A61B 5/7221* (2013.01); *A61B 5/7475* (2013.01); *A61B 17/3468* (2013.01);
(Continued)

(58) Field of Classification Search
CPC ............ A61N 1/37247; A61N 1/39622; A61N 1/025; A61N 1/3688; A61B 34/20; A61B 5/0006; A61B 5/04085; A61B 5/044; A61B 5/0452; A61B 5/6823; A61B 5/6843; A61B 5/7221; A61B 5/7475; A61B 17/3468; A61B 2034/2051; A61B 2562/0209; A61B 2562/043; A61B 2562/046
USPC ......................................................... 607/27
See application file for complete search history.

(56) References Cited

U.S. PATENT DOCUMENTS

| 4,233,987 A | 11/1980 | Feingold |
| 4,402,323 A | 9/1983 | White |

(Continued)

FOREIGN PATENT DOCUMENTS

| CN | 1043621 A | 11/1990 |
| CN | 1253761 A | 5/2000 |

(Continued)

OTHER PUBLICATIONS

U.S. Appl. No. 62/538,337, filed Jul. 28, 2017, Medtronic, Inc.
(Continued)

*Primary Examiner* — Carl H Layno
*Assistant Examiner* — Michael J Lau
(74) *Attorney, Agent, or Firm* — Mueting Raasch Group

(57) ABSTRACT

Systems, interfaces, and methods are described herein for evaluation and adjustment cardiac therapy. The systems, interfaces, and methods may utilize, or include, a graphical user interface to display various information with respect to a plurality of external electrodes and electrical activity monitored using such external electrodes and to allow a user to adjust what information to display.

28 Claims, 17 Drawing Sheets

(51) Int. Cl.
  *A61N 1/39* (2006.01)
  *A61B 5/00* (2006.01)
  *A61B 5/0408* (2006.01)
  *A61B 5/044* (2006.01)
  *A61B 5/0452* (2006.01)
  *A61B 17/34* (2006.01)
  *A61N 1/02* (2006.01)
  *A61N 1/365* (2006.01)
  *A61N 1/368* (2006.01)

(52) U.S. Cl.
  CPC .............. *A61B 34/20* (2016.02); *A61N 1/025* (2013.01); *A61N 1/3688* (2013.01); *A61N 1/36507* (2013.01); *A61N 1/39622* (2017.08); *A61B 2034/2051* (2016.02); *A61B 2562/0209* (2013.01); *A61B 2562/043* (2013.01); *A61B 2562/046* (2013.01)

(56) References Cited

U.S. PATENT DOCUMENTS

| | | |
|---|---|---|
| 4,428,378 A | 1/1984 | Anderson et al. |
| 4,497,326 A | 2/1985 | Curry |
| 4,566,456 A | 1/1986 | Koning et al. |
| 4,593,702 A | 6/1986 | Kepski |
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,810,740 A | 9/1998 | Paisner |
| 5,819,741 A * | 10/1998 | Karlsson ............... A61B 5/0006 600/523 |
| 5,876,336 A | 3/1999 | Swanson et al. |
| 5,891,045 A | 4/1999 | Albrecht et al. |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb et al. |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,238,158 B2 | 7/2007 | Abend |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harley et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |

(56) References Cited

U.S. PATENT DOCUMENTS

| | | |
|---|---|---|
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,731,642 B2 | 5/2014 | Zarkh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,861,830 B2 | 10/2014 | Brada et al. |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 9,474,457 B2 | 10/2016 | Ghosh et al. |
| 9,486,151 B2 | 11/2016 | Ghosh et al. |
| 9,510,763 B2 | 12/2016 | Gosh et al. |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,764,143 B2 | 9/2017 | Ghosh et al. |
| 9,776,009 B2 | 10/2017 | Ghosh et al. |
| 2002/0062087 A1* | 5/2002 | Anderson .......... A61B 5/04085 600/508 |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0243015 A1* | 12/2004 | Smith .................. A61B 5/4362 600/511 |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0167809 A1 | 7/2007 | Dala-Krishna |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0189701 A1* | 7/2010 | Cohen ................ C12N 15/1138 424/93.21 |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0130675 A1* | 6/2011 | Bibian ................ A61B 5/4064 600/544 |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |

(56) References Cited

U.S. PATENT DOCUMENTS

| | | |
|---|---|---|
| 2011/0213260 A1 | 9/2011 | Keel et al. |
| 2011/0313311 A1* | 12/2011 | Gaw ................... A61B 5/0536 600/547 |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1* | 12/2012 | Yuk ................... A61B 5/0408 600/547 |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1* | 11/2013 | George ............... A61B 5/04085 702/72 |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0114168 A1* | 4/2014 | Block ................ A61B 5/04001 600/393 |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1* | 10/2014 | Ghosh ................ A61B 5/044 600/510 |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0088225 A1* | 3/2015 | Noble ................. G06T 7/149 607/57 |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2015/0359491 A1 | 12/2015 | Smith et al. |
| 2016/0030747 A1 | 2/2016 | Thakur et al. |
| 2016/0030751 A1 | 2/2016 | Ghosh et al. |
| 2016/0045737 A1* | 2/2016 | Ghosh ................. A61B 5/0452 607/17 |
| 2016/0045738 A1 | 2/2016 | Ghosh et al. |
| 2016/0045744 A1 | 2/2016 | Gillberg et al. |
| 2016/0184590 A1 | 6/2016 | Ghosh |
| 2016/0235333 A1* | 8/2016 | Garber .................. A61B 5/742 |
| 2016/0331262 A1* | 11/2016 | Kuck .................. A61B 5/0464 |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | 2009065006 A2 | 5/2009 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

International Search Report and Written Opinion dated May 3, 2012 for International Application No. PCT/US2012/036262; 9 pages.
International Search Report and Written Opinion dated May 3, 2012 for International Application No. PCT/US2012/036302; 9 pages.
International Search Report and Written Opinion dated Aug. 6, 2014 for International Application No. PCT/US2014/036153; 14 pages.

(56) References Cited

OTHER PUBLICATIONS

International Search Report and Written Opinion dated Nov. 7, 2014 for International Application No. PCT/US2014/036163; 12 pages.
International Search Report and Written Opinion dated Oct. 28, 2014 for International Application No. PCT/US2014/041928; 15 pages.
International Search Report and Written Opinion dated Oct. 24, 2014 for International Application No. PCT/US2014/041929; 14 pages.
International Search Report and Written Opinion dated Nov. 4, 2014 for International Application No. PCT/US2014/0247583; 7 pages.
International Search Report and Written Opinion dated Nov. 12, 2014 for International Application No. PCT/US2014/047971; 7 pages.
International Search Report and Written Opinion dated Nov. 12, 2014 for International Application No. PCT/US2014/048120; 7 pages.
International Search Report and Written Opinion dated Mar. 9, 2015 for International Application No. PCT/US2014/069214; 11 pages.
International Search Report and Written Opinion dated Mar. 17, 2015, for International Application No. PCT/US2014/069192; 11 pages.
International Search Report and Written Opinion dated Mar. 16, 2015 for International Application No. PCT/US2014/069182; 11 pages.
International Search Report and Written Opinion dated Apr. 8, 2015 for International Application No. PCT/US2014/069070; 11 pages.
International Search Report and Written Opinion dated Jun. 11, 2015 for International Application No. PCT/US2015/021442; 13 pages.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
Botker MD, PhD., et al., "Electromechanical Mapping for Detection of Myocardial Viability in Patients with ischemia Cardiomyopathy," *Circulation*, Mar. 2001; vol. 103, No. 12, pp.
"CardioGuide System Enables Real-Time Navigation of Left Ventricular Leads During Medtronic CRT Implants," Press Release, Apr. 9, 2013, Medtronic, Inc., 2 pgs.
Cuculich, P.S., et al., "The Electrophysiological Cardiac Ventricular Substrate in Patients After Myocardial Infection" J. Am. Coll. Cardiol. 2011; 58:1893-1902.
Czerwinska et al., "Method of Segmentation of Thorax Organs Images Applied to Modeling the Cardiac Electrical Field," *Engineering in Medicine and Biology Society*, Proceedings of the $22^{nd}$ Annual International Conference of the IEEE, vol. 1, 23, Jul. 23, 2000.; pp. 402-405.
Dawoud, F. et al., "Inverse Electrocardiographic Imaging to Assess Electrical Dyssynchrony in Cardiac Resynchronization Therapy Patients," Computing in Cardiology, 2012; 39:993-996.
Freund et al., "A Decision-Theoretic Generalization of Online Learning and an Application to Boosting," *Journal of Computer and System Sciences*, 1997; 55(1):119-139.
Friedman, "Greedy Function Approximation: A Gradient Boosting Machine," *Annals of Statistics*, 2001; 29(5):1189-1232.
Friedman, "Stochastic Gradient Boosting," *Computational Statistics and Data Analysis*, 2002; 38(4):367-378.
Friedman et al., "Additive Logistic Regression: a Statistical View of Boosting," *Annals of Statistics*, 2000; 28(2):337-374.
Fung et al., Chapter 20, Optimization of Cardiac Resynchronization Therapy, Cardiac Resynchronization Therapy, Second Edition, Copyright 2008, Blackwell Publishing Ltd., pp. 356-373.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Gold et al., "Comparison of Stimulation Sites within Left Ventricular Veins on the Acute Hemodynamic Effects of Cardiac Resynchronization Therapy" *Heart Rhythm*, Apr. 2005; 2(4): 376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
Hayes et al., "Cardiac Resynchronization Therapy and the Relationship of Percent Biventricular Pacing to Symptoms and Survival," *Heart Rhythm*, Sep. 2011,; 8(9): 1469-1475.
"Heart Failure Management" datasheet [online]. Medtronic, Minneapolis, Minnesota, [Last updated on Jun. 3, 2013].Retrieved from the Internet: www.medtronic.com; 9 pages.
Hopenfeld et al., "The Effect of Conductivity on ST—Segment Epicardial Potentials Arising from Subendocardial Ischemia," Annals of Biomedical Eng., Jun. 2005; vol. 33, No. 6, pp. 751-763.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Lumason™, Brochure, Bracco Diagnostocs. Oct. 2014.
Medtronic Vitatron CARELINK ENCORE® Programmer Model 29901 Reference Manual, 2013, Medtronic, Inc., Minneapolis, MN.
Miri et al., "Applicability of body surface potential map in computerized optimization of biventricular pacing," Annals of Biomedical Engineering, vol. 38, No. 3, Mar. 2010, pp. 865-875.
Miri et al., "Comparison of the electrophysiologically based optimization methods with different pacing parameters in patient undergoing resynchronization treatment," 30th Annual International IEEE EMBS Conference, Aug. 2008, pp. 1741-1744.
Miri et al., "Computerized Optimization of Biventricular Pacing Using Body Surface Potential Map," 31st Annual International Conference of the IEEE EMBS, Sep. 2009, pp. 2815-2818.
Miri et al., "Efficiency of Timing Delays and Electrode Positions in Optimization of Biventricular Pacing: A Simulation Study," IEEE Transactions on Biomedical Engineering, Nov. 2009, pp. 2573-2582.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Nash et al., "An Experimental-Computational Framework for Validating in-vivo ECG Inverse Algorithms," International Journal of Bioelectromagnetism, vol. 2, No. 2, Dec. 31, 2000, 9 pp.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Ridgeway, "The State of Boosting," *Computing Science and Statistics*, 1999; 31:172-181.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.

(56) References Cited

OTHER PUBLICATIONS

Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms: a simulation study," Circulation Research, 1989, 64:449-462.
Strik et al., "Electrical and Mechanical Ventricular Activation During Left Bundle Branch Block and Resynchronization," *J. of Cardiovasc. Trans. Res.*, 2012; 5:117-126.
Svendsen et al., "Computational Models of Cardiac Electrical Activation," Chapter 5, Computational Nov. 2010, pp. 73-88.
Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010; 121(5):626-34. Available online Jan. 25, 2010.
Sweeney et al., QRS Fusion Complex Analysis Using Wave Interference to Predict Reverse Remodeling During Cardiac Resynchronization Therapy, heart Rhythm, 2014, 11:806-813.
Turner et al, "Electrical and Mechanical Components of Dyssynchrony in Heart Failure Patients with Normal QRS Duration and Left Bundle-Branch Block," *Circulation* 2004; 109:2544-2549.
Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.
Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.
Varma et al., "Placebo CRT," *Journal of Cardiovascular Electrophysiology*, vol. 19, Aug. 2008; p. 878.
Wang et al., "Application of the Method of Fundamental Solutions to Potential-based Inverse Electrocardiography," Annals of Biomedical Engineering, Aug. 2006, pp. 1272-1288.
Wellens, MD et al., "The Electrocardiogram 102 Years After Einthoven," Circulation, Feb. 2004; vol. 109, No. 5, pp. 562-564.
Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.
(PCT/US2019/034793) PCT Notification of Transmittal of the International Search Report and the Written Opinion of the International Searching Authority, dated Aug. 23, 2019, 11 pages.

\* cited by examiner

SYSTEMS, METHODS, AND INTERFACES FOR USE IN CARDIAC EVALUATION The disclosure herein relates to systems, methods, and interfaces for use in cardiac evaluation using external electrode apparatus.

Implantable medical devices (IMDs), such as implantable pacemakers, cardioverters, defibrillators, or pacemaker-cardioverter-defibrillators, provide therapeutic electrical stimulation to the heart. IMDs may provide pacing to address bradycardia, or pacing or shocks in order to terminate tachyarrhythmia, such as tachycardia or fibrillation. In some cases, the medical device may sense intrinsic depolarizations of the heart, detect arrhythmia based on the intrinsic depolarizations (or absence thereof), and control delivery of electrical stimulation to the heart if arrhythmia is detected based on the intrinsic depolarizations.

IMDs may also provide cardiac resynchronization therapy (CRT), which is a form of pacing. CRT involves the delivery of pacing to the left ventricle, or both the left and right ventricles. The timing and location of the delivery of pacing pulses to the ventricle(s) may be selected to improve the coordination and efficiency of ventricular contraction.

Systems for implanting medical devices may include workstations or other equipment in addition to the implantable medical device itself. In some cases, these other pieces of equipment assist the physician or other technician with placing the intracardiac leads at particular locations on or in the heart. In some cases, the equipment provides information to the physician about the electrical activity of the heart and the location of the intracardiac lead.

SUMMARY

The exemplary systems, methods, and interfaces described herein may be configured to assist a user (e.g., a physician) in evaluating a patient and evaluating cardiac therapy (e.g., cardiac therapy being performed on a patient during and/or after implantation of cardiac therapy apparatus). In one or more embodiments, the systems, methods, and interfaces may be described as being noninvasive. For example, in some embodiments, the systems, methods, and interfaces may not need, or include, implantable devices such as leads, probes, sensors, catheters, implantable electrodes, etc. to monitor, or acquire, a plurality of cardiac signals from tissue of the patient for use in evaluating the patient and/or cardiac therapy being delivered to the patient. Instead, the systems, methods, and interfaces may use electrical measurements taken noninvasively using, e.g., a plurality of external electrodes attached to the skin of a patient about the patient's torso.

It may be described that the illustrative systems, methods, and interfaces may be able to, or are configured to, display a live, or interactive, feedback on electrode connectivity with a three-state status. The three-state statuses may include not in contact, poor signal, or good signal. In at least one embodiment, one or more processes, or algorithms, may involve monitoring signal characteristics of each of the electrodes to determine the three-status state of the electrode. An illustrative graphical user interface may depict, or display, a graphical map of a plurality of electrode graphical elements, each corresponding to a physical, external electrode attached, or coupled, to the patient. An effectiveness value such as a three-state status value or indicator may be displayed proximate (e.g., within, next to, as part of, etc.) each of the electrode graphical elements such that, e.g., a user may quickly ascertain the effectiveness or status of each external electrode by viewing, or glancing upon, the illustrative graphical user interface.

Further, the illustrative systems, methods, and interfaces may include or may utilize one or more sorting processes, or algorithms, based on two or more metrics of electrical heterogeneity, or dyssynchrony, based on a plurality of external electrodes attached or coupled to the torso of a patient. For example, the processes may sort, or rank, cardiac resynchronization therapy settings based on improvements in the standard deviation of activation times (SDAT) and/or a statistic (e.g., average, media, etc.) of left ventricular activation times (LVAT) measured using the plurality of external electrodes. In at least one embodiment, SDAT may be used as the primary variable for sorting but, in case of two or more settings within a selected range (e.g., such as 3%) of SDAT improvement, LVAT may be further used to sort the two or more settings (e.g. to break the tie).

Still further, the illustrative systems, methods, and interfaces may include displaying electrode numbers on graphical maps of activation times and further indicating the electrodes where map data may have been interpolated due to missing signals. In one or more embodiments, activation times between two neighboring electrodes may be different due to lines of block, and an indication may be displayed on the graphical maps indicating the location of the block within the map. For example, adjacently-measured activation times may indicate a block if the activation times are different by a selected period of time (e.g., more than 50 milliseconds (ms)) (further, e.g., such adjacently-measured activation times may not be interpolated). The graphical map including lines of block may be used for implant guidance on where to place a lead.

The illustrative graphical user interfaces may be described as include a variety of different types of data displayed in a plurality of different ways. Some of the types of data may be indicative of the system status of the illustrative systems and methods described herein. For example, the illustrative graphical user interfaces may, or may be configured to, provide interactive feedback on status of electrode connection based on quality check of electrode signals, display the electrode layout on a torso model using different sizes of torso models fitting with different sized electrode apparatus (e.g., different sizes electrode belts or vest based on inputs of weight, height, gender, age, etc. to automatically select/ recommend the appropriate size), adjust the location of the external electrodes on the model to match locations as applied to the torso, e.g., based on user input of patient measurements such as, e.g., chest circumference measurements, and determine which external electrodes are not in good contact, based on low amplitude or baseline wander (e.g., processes, or algorithms, may be utilized to find the baseline used for the analysis).

The illustrative graphical user interfaces may, or may be configured to, display color-coded activation maps (e.g., two-dimensional maps, torso model maps, etc.) with external electrodes with invalid signals marked, which include areas on the map that are interpolated due to missing electrodes/invalid signals. The illustrative graphical user interfaces may, or may be configured to, to provide interpolation of electrical activation time data that is missing in areas based on activation times from neighboring electrodes or nearest neighbors with valid signals/activation times. Further, various criteria for invalid electrodes may be used to determine missing electrodes or electrodes with invalid signals. Electrode (ECG) signals from at least one or multitude of channels may be selectable either automatically or through user interaction. Further, the beat on which the data was processed and displayed may be indicated on the graphical user interface, and a user may have the ability to override automatic selection and pick a different beat.

The illustrative graphical user interfaces may, or may be configured to, include two planar views of the activation maps such as an anterior planar view and a posterior planar view. Further, three-dimensional (3D) views may also be provided or displayed such as a left-lateral 3D view and a right-lateral 3D view. Further, such 3D view may be rotatable either automatically or through user interaction with the interface.

The illustrative graphical user interfaces may, or may be configured to, include a summary screen that displays, or depict, activation maps of multiple different cardiac therapy settings with one or more options to rank selected cardiac therapy settings in order of improvement of electrical synchrony. Further, the summary screen could also include an activation map along with a physical map of lead pacing location. A user could select or input where the lead was placed or the electrode is pacing from (e.g., apical/mid-basal location in a posterior/posterior lateral/coronary sinus vein). The electrode apparatus and associated equipment may be wireless (e.g., Bluetooth communication) or wired communication with an implantable device, a programmer, and a tablet computer.

The illustrative systems, methods, and interfaces may further include an automated routine using a baseline (e.g., intrinsic or right ventricular pacing) rhythm of the patient and a left ventricle-only pacing and/or biventricular pacing at various atrioventricular and interventricular delays for different pacing vectors and sort settings (which, for example, may include a combination of timing and pacing vector). Processing and sensing circuitry including an amplifier may be described as collecting cardiac cycles simultaneously from the external electrodes and sending a chosen cardiac cycle for each setting to an implantable device or programmer for processing of activation times and determination of cardiac electrical dyssynchrony. In one example, the device may overdrive pace by a predetermined rate above the baseline rhythm for this evaluation.

The illustrative systems, methods, and interfaces may, or be configured to, sort selected settings according to improvements in metrics of electrical dyssynchrony such as, e.g., a standard deviation of activation times from all electrodes (SDAT) and average left ventricular activation time (LVAT). Further, certain settings may be automatically excluded in response to determination of high pacing thresholds and/or phrenic nerve stimulation.

In one or more embodiments, the cardiac therapy settings having, or with, a maximum reduction in SDAT and filters settings with SDAT reduction within 3% percentage points of the maximum reduction may be selected. Then, a maximum improvement in LVAT from the selected, or filtered, settings may be determined and the difference between LVAT improvements for each of the selected settings may be evaluated. Any setting that has an LVAT improvement that is less than about by 30% points or more (or another designated amount) may be excluded/demoted. All the remaining settings may then be considered as options for final programming of the cardiac therapy. Additionally, the sort settings may be further configured to optimize both device longevity and improvement from baseline, e.g., if two pacing sites are similarly beneficial hemodynamically, the pacing site with better device longevity may be selected. Conversely, if two pacing sites have similar device longevity, the one with better hemodynamics may be chosen.

It may be further described that the illustrative systems, methods, and interfaces may provide user with the means to record and save a five second ECG, SDAT, LVAT, and activation maps for intrinsic or RV paced rhythms. Further, the illustrative systems, methods, and interfaces may provide users with the means to record and save a 5 second ECG, % Δ in SDAT and LVAT from intrinsic or RV paced, and activation maps for various combinations of CRT settings (paced scenarios). Still further, the illustrative systems, methods, and interfaces may allow users to sort paced scenarios by % Δ in SDAT and LVAT from Intrinsic for each paced scenario, and may provide users with information to program the best CRT settings.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
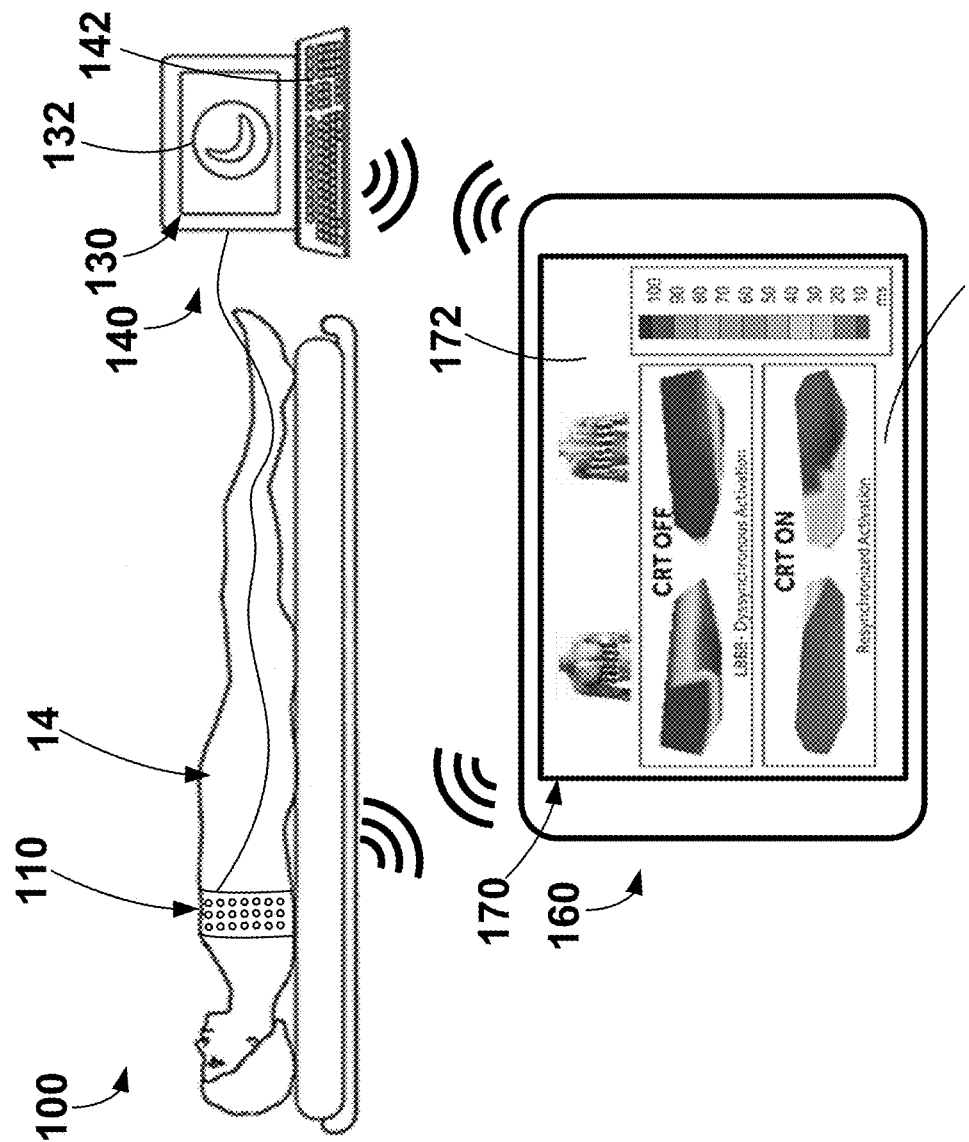
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, methods, and interfaces shall be described with reference to FIGS. 1-11. It will be apparent to one skilled in the art that elements or processes from one embodiment may be used in combination with elements or processes of the other embodiments, and that the possible embodiments of such systems, methods, and interfaces using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

A plurality of electrocardiogram (ECG) signals (e.g., torso-surface potentials) may be measured, or monitored, using a plurality of external electrodes positioned about the surface, or skin, of a patient. The ECG signals may be used to evaluate and configure cardiac therapy such as, e.g., cardiac therapy provide by an implantable medical device performing cardiac resynchronization therapy (CRT). As described herein, the ECG signals may be gathered or obtained noninvasively since, e.g., implantable electrodes may not be used to measure the ECG signals. Further, the ECG signals may be used to determine cardiac electrical activation times, which may be used to generate various metrics (e.g., electrical heterogeneity information) that may be used by a user (e.g., physician) to optimize one or more settings, or parameters, of cardiac therapy (e.g., pacing therapy) such as CRT.

Various exemplary systems, methods, and graphical user interfaces may be configured to use electrode apparatus including external electrodes, display apparatus, and computing apparatus to noninvasively assist a user (e.g., a physician) in the evaluation of cardiac health and/or the configuration (e.g., optimization) of cardiac therapy. An exemplary system 100 including electrode apparatus 110, computing apparatus 140, and a remote computing device 160 is depicted in FIG. 1.

The electrode apparatus 110 as shown includes a plurality of electrodes incorporated, or included, within a band wrapped around the chest, or torso, of a patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Exemplary electrode apparatus may be described in U.S. Pat. No. 9,320,446 entitled "Bioelectric Sensor Device and Methods" filed Mar. 27, 2014 and issued on Mar. 26, 2016, which is incorporated herein by reference in its entirety. Further, exemplary electrode apparatus 110 will be described in more detail in reference to FIGS. 2-3.

Although not described herein, the exemplary system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the exemplary systems, methods, and interfaces described herein may further use imaging apparatus to provide noninvasive assistance to a user (e.g., a physician) to locate, or place, one or more pacing electrodes proximate the patient's heart in conjunction with the configuration of cardiac therapy.

For example, the exemplary systems and methods may provide image guided navigation that may be used to navigate leads including electrodes, leadless electrodes, wireless electrodes, catheters, etc., within the patient's body while also providing noninvasive cardiac therapy configuration including determining an effective, or optimal, LVAD parameters A-V interval, etc. Exemplary systems and methods that use imaging apparatus and/or electrode apparatus may be described in U.S. Pat. App. Pub. No. 2014/0371832 to Ghosh published on Dec. 18, 2014, U.S. Pat. App. Pub. No. 2014/0371833 to Ghosh et al. published on Dec. 18, 2014, U.S. Pat. App. Pub. No. 2014/0323892 to Ghosh et al. published on Oct. 30, 2014, U.S. Pat. App. Pub. No. 2014/0323882 to Ghosh et al. published on Oct. 20, 2014, each of which is incorporated herein by reference in its entirety.

Exemplary imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate implantable apparatus to target locations within the heart or other areas of interest.

Systems and/or imaging apparatus that may be used in conjunction with the exemplary systems and method described herein are described in U.S. Pat. App. Pub. No. 2005/0008210 to Evron et al. published on Jan. 13, 2005, U.S. Pat. App. Pub. No. 2006/0074285 to Zarkh et al.

published on Apr. 6, 2006, U.S. Pat. No. 8,731,642 to Zarkh et al. issued on May 20, 2014, U.S. Pat. No. 8,861,830 to Brada et al. issued on Oct. 14, 2014, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The computing apparatus 140 and the remote computing device 160 may each include display apparatus 130, 160, respectively, that may be configured to display and analyze data such as, e.g., electrical signals (e.g., electrocardiogram data), electrical activation times, electrical heterogeneity information, etc. For example, one cardiac cycle, or one heartbeat, of a plurality of cardiac cycles, or heartbeats, represented by the electrical signals collected or monitored by the electrode apparatus 110 may be analyzed and evaluated for one or more metrics including activation times and electrical heterogeneity information that may be pertinent to the therapeutic nature of one or more parameters related to cardiac therapy such as, e.g., pacing parameters, lead location, etc. More specifically, for example, the QRS complex of a single cardiac cycle may be evaluated for one or more metrics such as, e.g., QRS onset, QRS offset, QRS peak, electrical heterogeneity information, electrical activation times, left ventricular or thoracic standard deviation of electrical activation times (LVED), standard deviation of activation-times (SDAT), average left ventricular or thoracic surrogate electrical activation times (LVAT), referenced to earliest activation time, QRS duration (e.g., interval between QRS onset to QRS offset), difference between average left surrogate and average right surrogate activation times, relative or absolute QRS morphology, difference between a higher percentile and a lower percentile of activation times (higher percentile may be 90%, 80%, 75%, 70%, etc. and lower percentile may be 10%, 15%, 20%, 25% and 30%, etc.), other statistical measures of central tendency (e.g., median or mode), dispersion (e.g., mean deviation, standard deviation, variance, interquartile deviations, range), etc. Further, each of the one or more metrics may be location specific. For example, some metrics may be computed from signals recorded, or monitored, from electrodes positioned about a selected area of the patient such as, e.g., the left side of the patient, the right side of the patient, etc.

In at least one embodiment, one or both of the computing apparatus 140 and the remote computing device 160 may be a server, a personal computer, or a tablet computer. The computing apparatus 140 may be configured to receive input from input apparatus 142 (e.g., a keyboard) and transmit output to the display apparatus 130, and the remote computing device 160 may be configured to receive input from input apparatus 162 (e.g., a touchscreen) and transmit output to the display apparatus 170. One or both of the computing apparatus 140 and the remote computing device 160 may include data storage that may allow for access to processing programs or routines and/or one or more other types of data, e.g., for analyzing a plurality of electrical signals captured by the electrode apparatus 110, for determining QRS onsets, QRS offsets, medians, modes, averages, peaks or maximum values, valleys or minimum values, for determining electrical activation times, for driving a graphical user interface configured to noninvasively assist a user in configuring one or more pacing parameters, or settings, such as, e.g., pacing rate, ventricular pacing rate, A-V interval, V-V interval, pacing pulse width, pacing vector, multipoint pacing vector (e.g., left ventricular vector quad lead), pacing voltage, pacing configuration (e.g., biventricular pacing, right ventricle only pacing, left ventricle only pacing, etc.), and arrhythmia detection and treatment, rate adaptive settings and performance, etc. Further, in at least one embodiment, one or both of the computing apparatus 140 and the remote computing device 160 may include data storage that may allow for access to processing programs or routines and/or one or more other types of data, e.g., for driving a graphical user interface configured to noninvasively assist a user in configuring one or more cardiac therapy parameters, or settings, such LVAD pump speed, LVAD pump throughput, LVAD pump power, LVAD pump current, pump inflow gimbal angle, automatic algorithmic responses to events such as pump suction, patient activity level changes, and physiologic parameter inputs, enabling/disabling periodic pump speed modulation features such as the Lavare cycle.

The computing apparatus 140 may be operatively coupled to the input apparatus 142 and the display apparatus 130 to, e.g., transmit data to and from each of the input apparatus 142 and the display apparatus 130, and the remote computing device 160 may be operatively coupled to the input apparatus 162 and the display apparatus 170 to, e.g., transmit data to and from each of the input apparatus 162 and the display apparatus 170. For example, the computing apparatus 140 and the remote computing device 160 may be electrically coupled to the input apparatus 142, 162 and the display apparatus 130, 170 using, e.g., analog electrical connections, digital electrical connections, wireless connections, bus-based connections, network-based connections, internet-based connections, etc. As described further herein, a user may provide input to the input apparatus 142, 162 to view and/or select one or more pieces of configuration information related to the cardiac therapy delivered by cardiac therapy apparatus such as, e.g., an implantable medical device.

Although as depicted the input apparatus 142 is a keyboard and the input apparatus 162 is a touchscreen, it is to be understood that the input apparatus 142, 162 may include any apparatus capable of providing input to the computing apparatus 140 and the computing device 160 to perform the functionality, methods, and/or logic described herein. For example, the input apparatus 142, 162 may include a keyboard, a mouse, a trackball, a touchscreen (e.g., capacitive touchscreen, a resistive touchscreen, a multi-touch touchscreen, etc.), etc. Likewise, the display apparatus 130, 170 may include any apparatus capable of displaying information to a user, such as a graphical user interface 132, 172 including electrode status information, graphical maps of electrical activation, a plurality of signals for the external electrodes over one or more heartbeats, QRS complexes, various cardiac therapy scenario selection regions, various rankings of cardiac therapy scenarios, various pacing parameters, electrical heterogeneity information, textual instructions, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130, 170 may include a liquid crystal display, an organic light-emitting diode screen, a touchscreen, a cathode ray tube display, etc.

The processing programs or routines stored and/or executed by the computing apparatus 140 and the remote computing device 160 may include programs or routines for computational mathematics, matrix mathematics, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing used to implement one or more exemplary methods and/or processes described herein. Data stored and/or used by the computing apparatus 140 and the remote computing device 160 may include, for example, electrical signal/waveform data from the electrode apparatus 110 (e.g., a plurality of QRS complexes), electrical activation times from the electrode apparatus 110, cardiac sound/signal/waveform data from acoustic sensors, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, electrical heterogeneity information, etc.), or any other data that may be used for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and interfaces may be implemented using a computer readable storage medium, configured with a computer program, where the storage medium so configured causes the computer to operate in a specific and predefined manner to perform functions described herein. Further, in at least one embodiment, the exemplary systems, methods, and interfaces may be described as being implemented by logic (e.g., object code) encoded in one or more non-transitory media that includes code for execution and, when executed by a processor or processing circuitry, is operable to perform operations such as the methods, processes, and/or functionality described herein.

The computing apparatus 140 and the remote computing device 160 may be, for example, any fixed or mobile computer system (e.g., a controller, a microcontroller, a personal computer, minicomputer, tablet computer, etc.). The exact configurations of the computing apparatus 140 and the remote computing device 160 are not limiting, and essentially any device capable of providing suitable computing capabilities and control capabilities (e.g., signal analysis, mathematical functions such as medians, modes, averages, maximum value determination, minimum value determination, slope determination, minimum slope determination, maximum slope determination, graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by the computing apparatus 140 and the remote computing device 160 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein.

Figure 2:
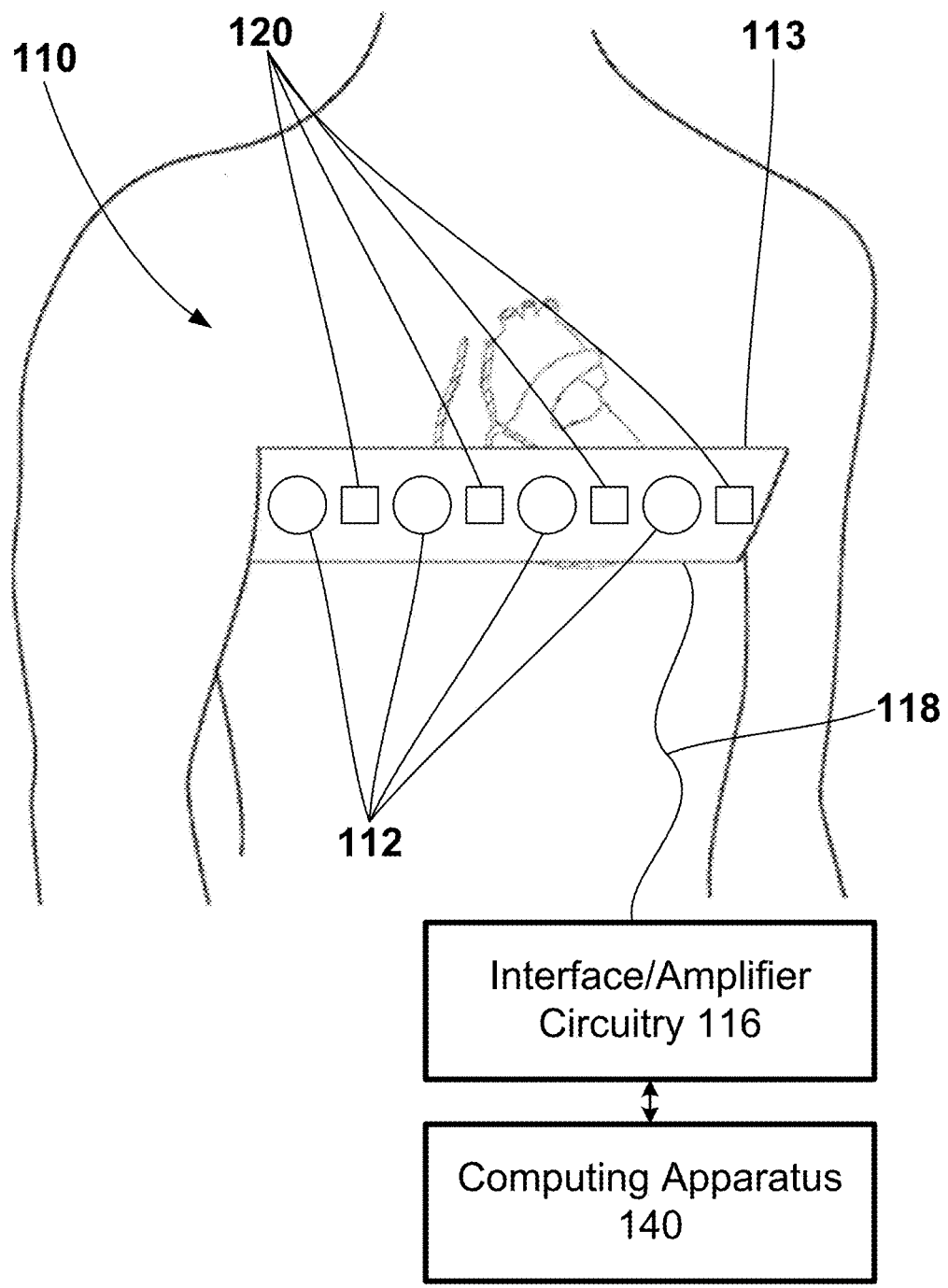
FIGS. 2-3 are diagrams of exemplary external electrode apparatus for measuring torso-surface potentials.

The exemplary electrode apparatus 110 may be configured to measure body-surface potentials of a patient 14 and, more particularly, torso-surface potentials of a patient 14. As shown in FIG. 2, the exemplary electrode apparatus 110 may include a set, or array, of external electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, anterolateral, and anterior locations of the torso of a patient 14.

The exemplary electrode apparatus 110 may be further configured to measure, or monitor, sounds from at least one or both the patient 14. As shown in FIG. 2, the exemplary electrode apparatus 110 may include a set, or array, of acoustic sensors 120 attached, or coupled, to the strap 113. The strap 113 may be configured to be wrapped around the torso of a patient 14 such that the acoustic sensors 120 surround the patient's heart. As further illustrated, the acoustic sensors 120 may be positioned around the circumference of a patient 14, including the posterior, lateral, posterolateral, anterolateral, and anterior locations of the torso of a patient 14.

Further, the electrodes 112 and the acoustic sensors 120 may be electrically connected to interface/amplifier circuitry 116 via wired connection 118. The interface/amplifier circuitry 116 may be configured to amplify the signals from the electrodes 112 and the acoustic sensors 120 and provide the signals to one or both of the computing apparatus 140 and the remote computing device 160. Other exemplary systems may use a wireless connection to transmit the signals sensed by electrodes 112 and the acoustic sensors 120 to the interface/amplifier circuitry 116 and, in turn, to one or both of the computing apparatus 140 and the remote computing device 160, e.g., as channels of data. In one or more embodiments, the interface/amplifier circuitry 116 may be electrically coupled to the computing apparatus 140 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112 and the acoustic sensors 120. In some examples, the strap 113 may include an elastic band, strip of tape, or cloth. Further, in some examples, the strap 113 may be part of, or integrated with, a piece of clothing such as, e.g., a t-shirt. In other examples, the electrodes 112 and the acoustic sensors 120 may be placed individually on the torso of a patient 14. Further, in other examples, one or both of the electrodes 112 (e.g., arranged in an array) and the acoustic sensors 120 (e.g., also arranged in an array) may be part of, or located within, patches, vests, and/or other manners of securing the electrodes 112 and the acoustic sensors 120 to the torso of the patient 14. Still further, in other examples, one or both of the electrodes 112 and the acoustic sensors 120 may be part of, or located within, two sections of material or two patches. One of the two patches may be located on the anterior side of the torso of the patient 14 (to, e.g., monitor electrical signals representative of the anterior side of the patient's heart, measure surrogate cardiac electrical activation times representative of the anterior side of the patient's heart, monitor or measure sounds of the anterior side of the patient, etc.) and the other patch may be located on the posterior side of the torso of the patient 14 (to, e.g., monitor electrical signals representative of the posterior side of the patient's heart, measure surrogate cardiac electrical activation times representative of the posterior side of the patient's heart, monitor or measure sounds of the posterior side of the patient, etc.). And still further, in other examples, one or both of the electrodes 112 and the acoustic sensors 120 may be arranged in a top row and bottom row that extend from the anterior side of the patient 14 across the left side of the patient 14 to the anterior side of the patient 14. Yet still further, in other examples, one or both of the electrodes 112 and the acoustic sensors 120 may be arranged in a curve around the armpit area and may have an electrode/sensor-density that less dense on the right thorax that the other remaining areas.

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing.

In some examples, there may be about 12 to about 50 electrodes 112 and about 12 to about 50 acoustic sensors 120 spatially distributed around the torso of a patient. Other configurations may have more or fewer electrodes 112 and more or fewer acoustic sensors 120. It is to be understood that the electrodes 112 and acoustic sensors 120 may not be arranged or distributed in an array extending all the way around or completely around the patient 14. Instead, the electrodes 112 and acoustic sensors 120 may be arranged in an array that extends only part of the way or partially around the patient 14. For example, the electrodes 112 and acoustic sensors 120 may be distributed on the anterior, posterior, and left sides of the patient with less or no electrodes and acoustic sensors proximate the right side (including posterior and anterior regions of the right side of the patient).

The computing apparatus 140 may record and analyze the torso-surface potential signals sensed by electrodes 112 and the sound signals sensed by the acoustic sensors 120, which are amplified/conditioned by the interface/amplifier circuitry 116. The computing apparatus 140 may be configured to analyze the electrical signals from the electrodes 112 to provide electrocardiogram (ECG) signals, information, or data from the patient's heart as will be further described herein. The computing apparatus 140 may be configured to analyze the electrical signals from the acoustic sensors 120 to provide sound signals, information, or data from the patient's body and/or devices implanted therein (such as a left ventricular assist device).

Additionally, the computing apparatus 140 and the remote computing device 160 may be configured to provide graphical user interfaces 132, 172 depicting various information related to the electrode apparatus 110 and the data gathered, or sensed, using the electrode apparatus 110. For example, the graphical user interfaces 132, 172 may depict ECGs including QRS complexes obtained using the electrode apparatus 110 and sound data including sound waves obtained using the acoustic sensors 120 as well as other information related thereto. Exemplary systems and methods may noninvasively use the electrical information collected using the electrode apparatus 110 and the sound information collected using the acoustic sensors 120 to evaluate a patient's cardiac health and to evaluate and configure cardiac therapy being delivered to the patient.

Further, the electrode apparatus 110 may further include reference electrodes and/or drive electrodes to be, e.g. positioned about the lower torso of the patient 14, that may be further used by the system 100. For example, the electrode apparatus 110 may include three reference electrodes, and the signals from the three reference electrodes may be combined to provide a reference signal. Further, the electrode apparatus 110 may use of three caudal reference electrodes (e.g., instead of standard references used in a Wilson Central Terminal) to get a "true" unipolar signal with lesser noise from averaging three caudally located reference signals.

Figure 3:
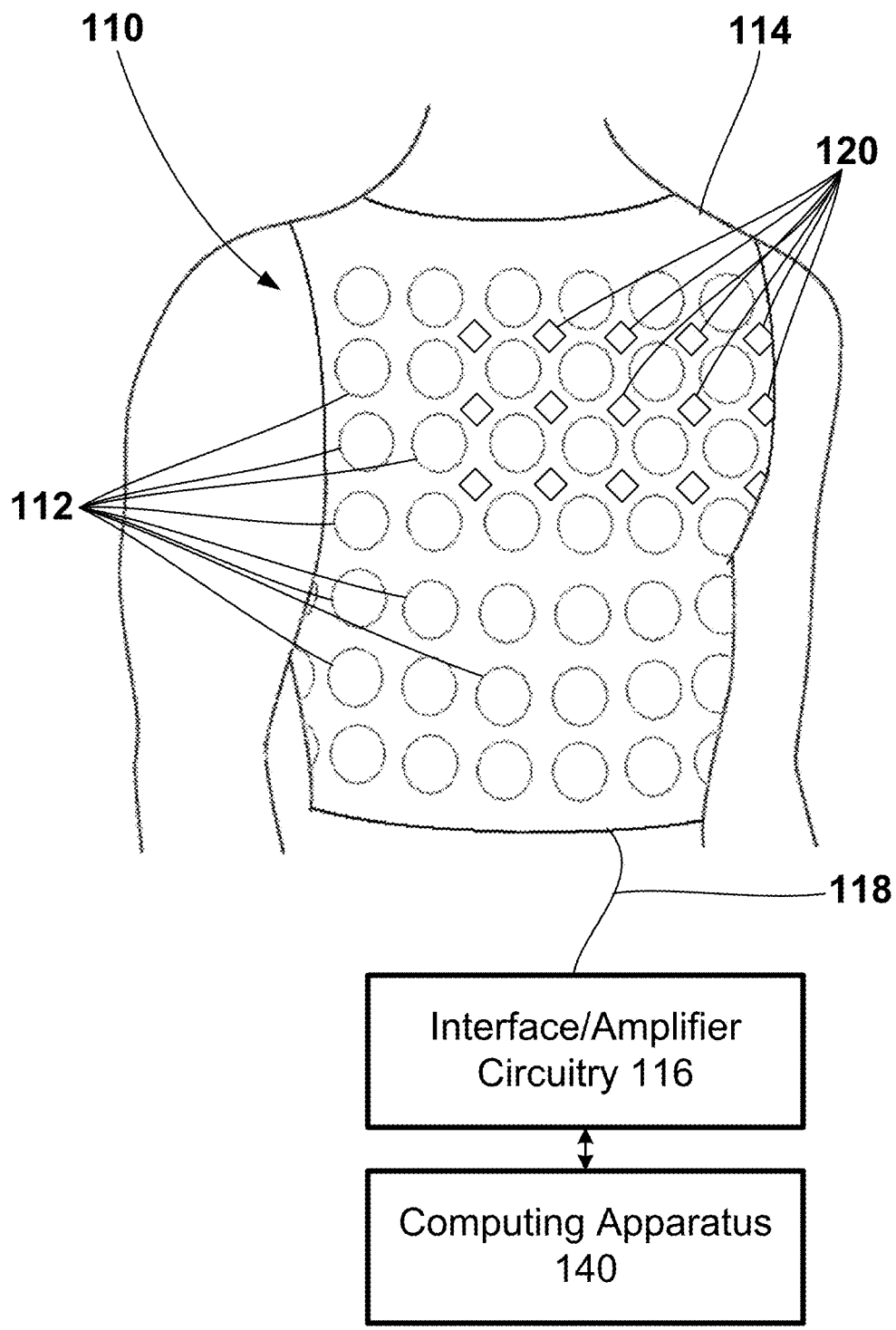

FIG. 3 illustrates another exemplary electrode apparatus 110 that includes a plurality of electrodes 112 configured to surround the heart of the patient 14 and record, or monitor, the electrical signals associated with the depolarization and repolarization of the heart after the signals have propagated through the torso of the patient 14 and a plurality of acoustic sensors 120 configured to surround the heart of the patient 14 and record, or monitor, the sound signals associated with the heart and/or an implanted device such as the LVAD after the signals have propagated through the torso of the patient 14. The electrode apparatus 110 may include a vest 114 upon which the plurality of electrodes 112 and the plurality of acoustic sensors 120 may be attached, or to which the electrodes 112 and the acoustic sensors 120 may be coupled.

In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 and the acoustic sensors 120 through a wired connection 118 and be configured to transmit signals from the electrodes 112 and the acoustic sensors 120 to computing apparatus 140. As illustrated, the electrodes 112 and the acoustic sensors 120 may be distributed over the torso of a patient 14, including, for example, the posterior, lateral, posterolateral, anterolateral, and anterior locations of the torso of a patient 14.

The vest 114 may be formed of fabric with the electrodes 112 and the acoustic sensors 120 attached to the fabric. The vest 114 may be configured to maintain the position and spacing of electrodes 112 and the acoustic sensors 120 on the torso of the patient 14. Further, the vest 114 may be marked to assist in determining the location of the electrodes 112 and the acoustic sensors 120 on the surface of the torso of the patient 14. In some examples, there may be about 25 to about 256 electrodes 112 and about 25 to about 256 acoustic sensors 120 distributed around the torso of the patient 14, though other configurations may have more or fewer electrodes 112 and more or fewer acoustic sensors 120.

The exemplary systems and methods may be used to provide noninvasive assistance to a user in the evaluation of a patient's cardiac health and/or evaluation and configuration of cardiac therapy being presently-delivered to the patient (e.g., by an implantable medical device, by a LVAD, etc.). For example, the exemplary systems and methods may be used to assist a user in the configuration and/or adjustment of one or more cardiac therapy settings such as, e.g., optimization of the A-V interval, or delay, of pacing therapy (e.g., left univentricular pacing therapy). Further, for example, the exemplary systems and methods may be used to assist a user in the configuration and/or adjustment of one or more cardiac therapy settings for LVAD-delivered cardiac therapy.

Further, it is to be understood that the computing apparatus 140 and the remote computing device 160 may be operatively coupled to each other in a plurality of different ways so as to perform, or execute, the functionality described herein. For example, in the embodiment depicted, the computing device 140 may be wireless operably coupled to the remote computing device 160 as depicted by the wireless signal lines emanating therebetween. Additionally, as opposed to wireless connections, one or more of the computing apparatus 140 and the remoting computing device 160 may be operably coupled through one or wired electrical connections.

Illustrative graphical user interfaces that may be used to monitor information related to or gathered using the electrode apparatus (e.g., external electrodes about a patient's torso) described herein are depicted in FIGS. 4-8. For example, each of the graphical user interfaces of FIGS. 4-8 may be displayed, or depicted, on the graphical user interfaces 132, 172 of the displays 130, 170 of the computing apparatus 140 and the remote computing device 150.

Figure 4:
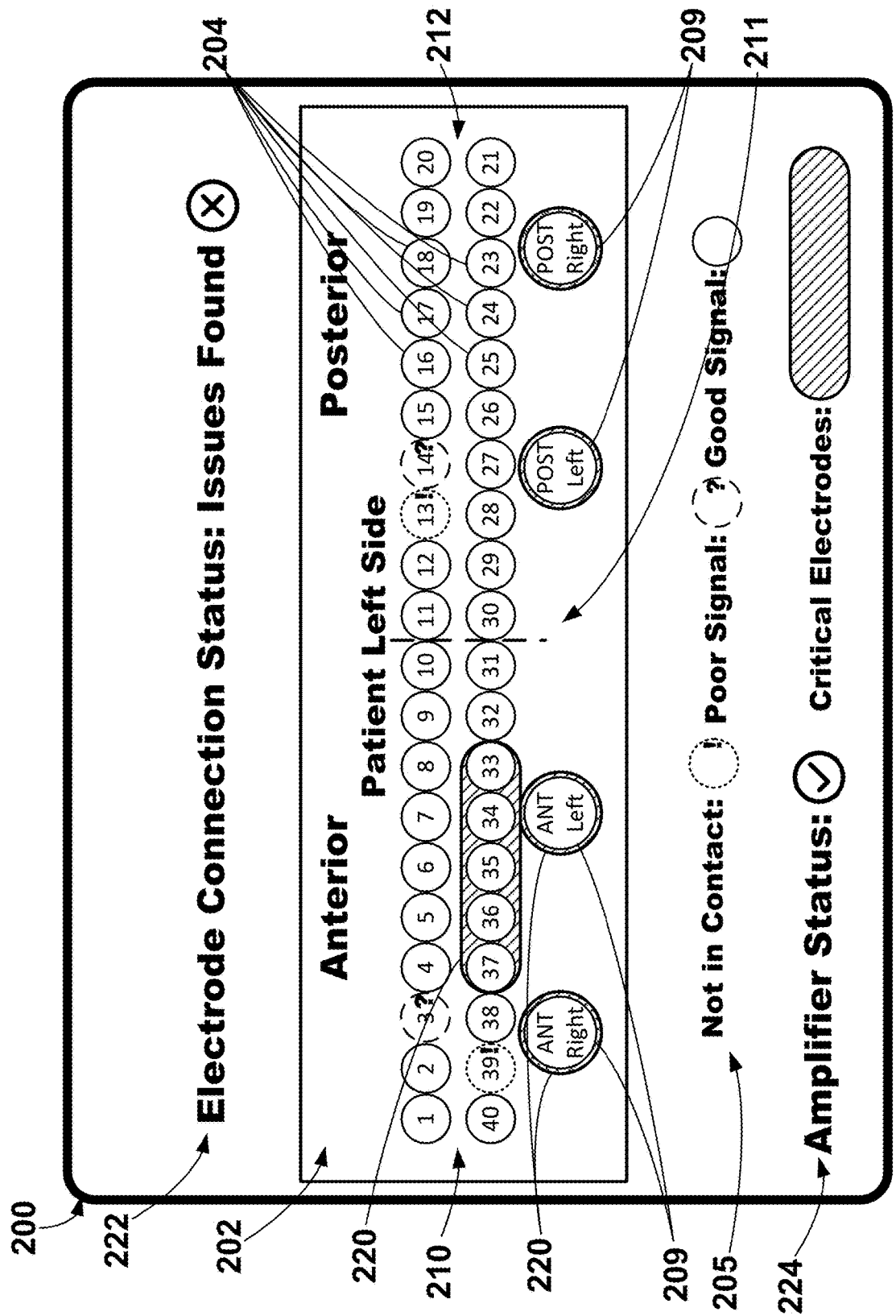
FIG. 4 is an illustrative graphical user interface depicting electrode status information, e.g., for use with the systems and external electrode apparatus of FIGS. 1-3.

An illustrative graphical user interface 200 depicting electrode status information is depicted in FIG. 4. The graphical user interface 200 may include, among other things, a graphical electrode map 202 depicting information related to each of the physical electrodes of the electrode apparatus described herein with respect to FIGS. 1-3. More specifically, in this embodiment, the graphical electrode map 202 includes a plurality of electrode graphical elements 204 (some which are labeled in FIG. 4) corresponding to and positioned on the graphical map 202 in relation to the physical location of the physical electrodes located proximate the patient's skin. Although, in this embodiment, each electrode graphical element 204 is generally represented by a circle, it is to be understood that different graphics, or graphical representations, may be used to represent each physical electrode.

Each electrode graphical 204 may include a number within a circle, which may correspond to a number printed on each of the physical electrodes. As shown, the graphical electrode elements 204 are numbered one through forty. Further, the graphical electrode map 204 may further include one or more graphical reference electrode elements 209 that correspond to physical reference electrodes. As shown, four graphical reference electrode elements 209 are depicted on the graphical electrode map 202: more specifically, an anterior right side graphical reference electrode element, an anterior left side graphical reference electrode element, a posterior right side graphical reference electrode element, and a posterior right side graphical reference electrode element.

In this embodiment, the graphical electrode map 202 may extend from a left portion 210 to a right portion 212. A middle portion 211 may be located between the left portion 210 and the right portion 212. The left portion 210 may correspond to the anterior side of the patient, the right portion 212 may correspond to the posterior side of the patient, and the middle portion 211 may correspond to the left side of the patient. In other words, the graphical map 202 visually represent the physical electrodes wrapping around the patient from the anterior to the patient's left side to the patient's posterior.

Each electrode graphical element 204 may correspond to a physical electrode of the electrode apparatus described herein with respect to FIGS. 1-3. Due to various reasons (e.g., malfunction, poor contact, etc.), the physical electrodes may not provide an adequate, or acceptable, signal to be effectively used to derive electrical activity from the patient to be used in cardiac evaluation and cardiac therapy evaluation and adjustment. Each electrode graphical element 204 as well as the reference electrode graphical elements 209 may provide an effectiveness value proximate thereto to, for example, indicate or represent the effectiveness of the corresponding physical electrode in providing a valid sensing signal from the tissue of the patient.

In this embodiment, each electrode graphical element 204 may have one of three different effectiveness values. In other words, each of the electrode graphical elements may have one of three states to indicate the effectiveness of the corresponding physical electrode in providing a valid sensing signal from the tissue of the patient. A physical electrode that is not in contact with tissue so as to not provide a valid sensing signal may be represented by a dotted-line circle and an exclamation mark positioned within the dotted-line circle. A physical electrode that is in contact with tissue but provides a poor signal so has to not provide a valid sensing signal may be represented by a dashed-line circle and a question mark positioned within the dashed-line circle. A physical electrode that is in contact with tissue so as to provide a valid sensing signal may be represented by a solid-line circle. As shown, electrodes 3 and 14 have poor signal, and thus, the corresponding electrode graphical elements 204 are dashed-line circles with a question mark positioned within the dashed-line circles. Further, electrodes 13 and 39 are not in contact (e.g., no signal), and thus, the corresponding electrode graphical elements 204 are dotted-line circles with an exclamation mark positioned within the dotted-line circles.

In other embodiments, the effectiveness values may be represented using different graphics, or graphical representations, or using different colors or animations. For example, a physical electrode that is not in contact with tissue so as to not provide a valid sensing signal may be represented by a red circle, a physical electrode that is in contact with tissue but provides a poor signal so as to not provide a valid sensing signal may be represented by a yellow circle, and a physical electrode that is in contact with tissue so as to provide a valid sensing signal may be represented by a green circle.

In one example, more specifically, determination of the ECG signals that should be flagged as "red" or "yellow" on the system status screen may be accomplished by creating a series of 1-second windows and removing any signals that are "lead off" per the amplifier at any measured point during a 1-second window. If they are "lead off" in at least 2 of 3 consecutive windows, then such signals may be flagged as "red." Next, the remaining signals may be de-trended using various processes. Then, within each 1-second window, any signals with peak-to-peak amplitude <0.12 millivolts (mV) may be removed and flagged as "potential yellow." Further, the standard deviation across all remaining signals at each time point may be calculated, and the standard deviation slope at each time point=absolute value difference between successive standard deviations may also be calculated. Using a 200 ms rolling window, the area under the curve of the standard deviation slopes may be determined, and 200 ms window with the minimum area under the curve may be identified or found. Within the 200 ms window, a rolling 100 ms window may be used to calculate the area under the curve of the standard deviation slopes, and the 100 ms window with the minimum area under the curve may be identified or found. Still further, the peak-to-peak amplitude of each signal in the 100 ms window may be calculated, and any remaining signals with peak-to-peak amplitude >2.5*median peak-to-peak amplitude may be flagged as "potential yellow." For each series of 3 consecutive windows, the remaining signals flagged as "potential yellow" may be identified in at least 2 windows and flagged as "yellow."

Further, determination of whether the electrode status is acceptable for recording and calculating metrics/activation maps may be accomplished through the following processes. First, exclude any electrode that is indicated as "lead off" or poor signal. Second, exclude any electrode where both neighbors were excluded in the first step. Third, if any of the following conditions are true, electrode contact is "unacceptable": any reference electrode or the drive electrode is indicated as "lead-off" per the amplifier; more than two of electrodes 1-4 and 37-40 are excluded; more than two of electrodes 5-8 and 33-36 are excluded; more than two of electrodes 9-12 and 29-32 are excluded; more than two of electrodes 13-16 and 25-28 are excluded; more than two of electrodes 17-24 are excluded; more than one of electrodes 33-37 are excluded. If none of those conditions are true the electrode contact for the system may be considered "acceptable."

A key 205 may be provided on the graphical user interface 200 proximate the graphical electrode map 202 to provide examples of the various effectiveness values, or states, of the electrode graphical elements 204. As shown, the key 205 includes one of each of different effectiveness values in this example: not in contact, poor signal, and good signal.

The graphical electrode map 202 may further include, or define, one or more principle electrodes graphical regions 220 to indicate which of the electrode graphical elements 204 correspond to physical electrodes that are considered to be the most principle electrodes (e.g., important electrodes, critical electrodes, etc.). In this example, the principle electrodes graphical regions 220 may include a cross-hatched, or shaded, background about the electrode graphical elements 204 corresponding to the most significant electrodes. In other words, the principal electrodes graphical regions 220 may be referred to as critical electrodes regions to indicate which of the physical electrodes may be critical to obtaining electrical activity signals, or data, from the patient to evaluate the patient's cardiac health and cardiac therapy being delivered to the patient.

As shown, the principle electrodes graphical region 220 has identified five electrode graphical elements 204 corresponding to physical electrodes positioned proximate the patient's left-central anterior. These physical electrodes may be determined to be significant because they provide the most significant electrical signals from the patient for use in evaluating the patient's cardiac health and cardiac therapy being delivered to the patient. The key 205, as shown, may further provide an example of the principle electrode regions. In this example, the principle electrode regions may be referred to as "Critical Electrodes." In one or more embodiments, one or more (e.g., all) of the plurality of reference electrodes may be considered to be principle electrodes, and thus, a principle electrodes graphical region 220 may be positioned about the reference electrode graphical elements 209.

Additionally, the illustrative graphical user interface 200 may include a global electrode connection status message 222 indicative of the state of the plurality of physical electrodes providing valid sensing signal from the tissue of the patient. The global electrode connection status message 222 may be generated by determining how many of the physical electrodes are providing a good signal versus how many of the physical electrodes are providing a poor signal or are not in contact. If a selected number of the physical electrodes are determined as providing a good signal, the global electrode connection status message 222 may provide a message such as, e.g., "Good Contact" and a checkmark within a circle. As shown, if a selected number of the physical electrodes are determined as not providing a good signal, the global electrode connection status message 222 may provide a message such as, e.g., "Issues Found" and a "X" within a circle. Still further, the illustrative graphical user interface 200 may include an amplifier status indicator 224. As shown, the amplifier status indicator 224 has a checkmark within a circle to indicate that the amplifier is connected and working properly.

Figure 5A:
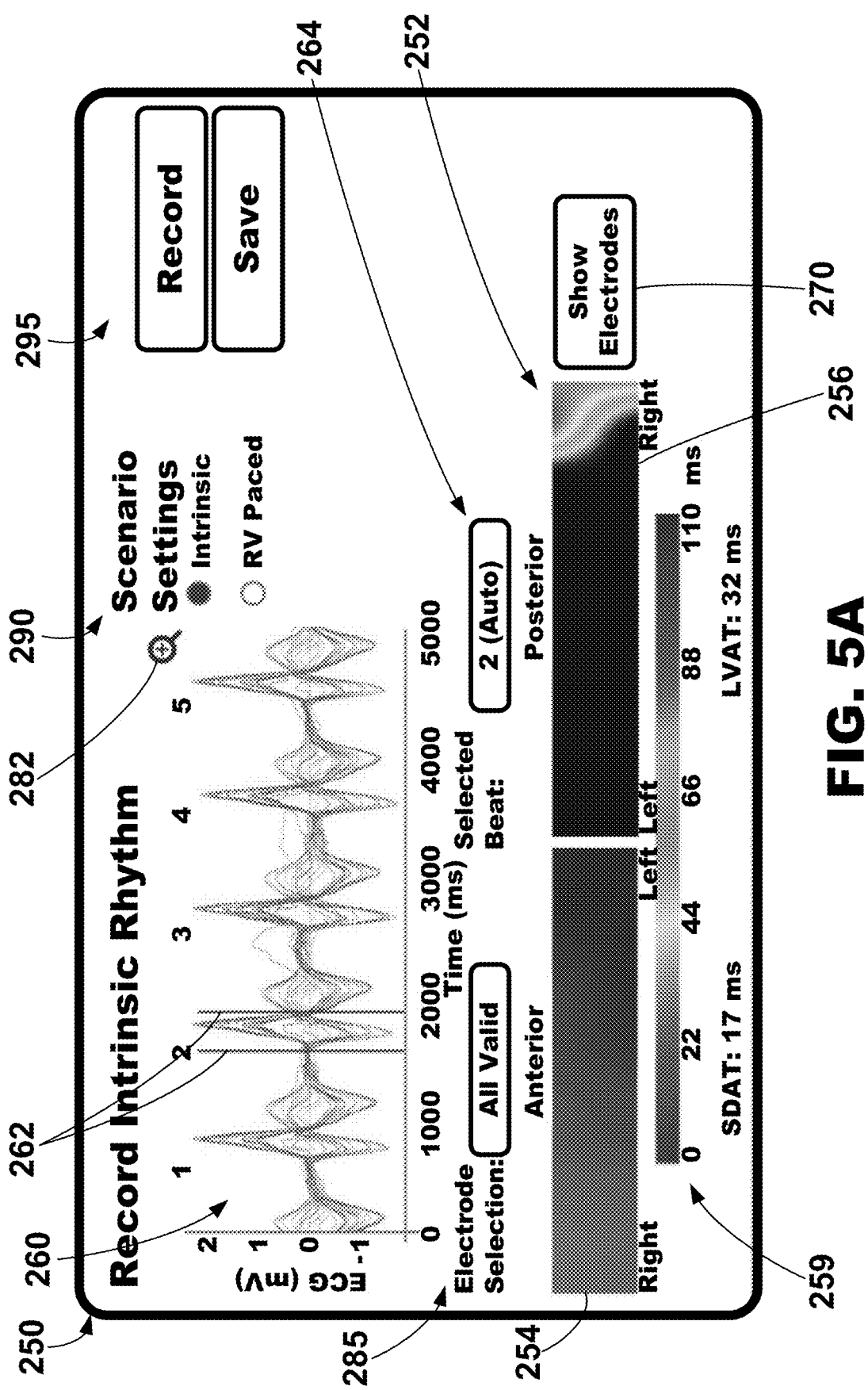
FIGS. 5A-5B are illustrative graphical user interfaces depicting, among other things, a graphical map of electrical activation, e.g., for use with the systems and external electrode apparatus of FIGS. 1-3.
Figure 5B:
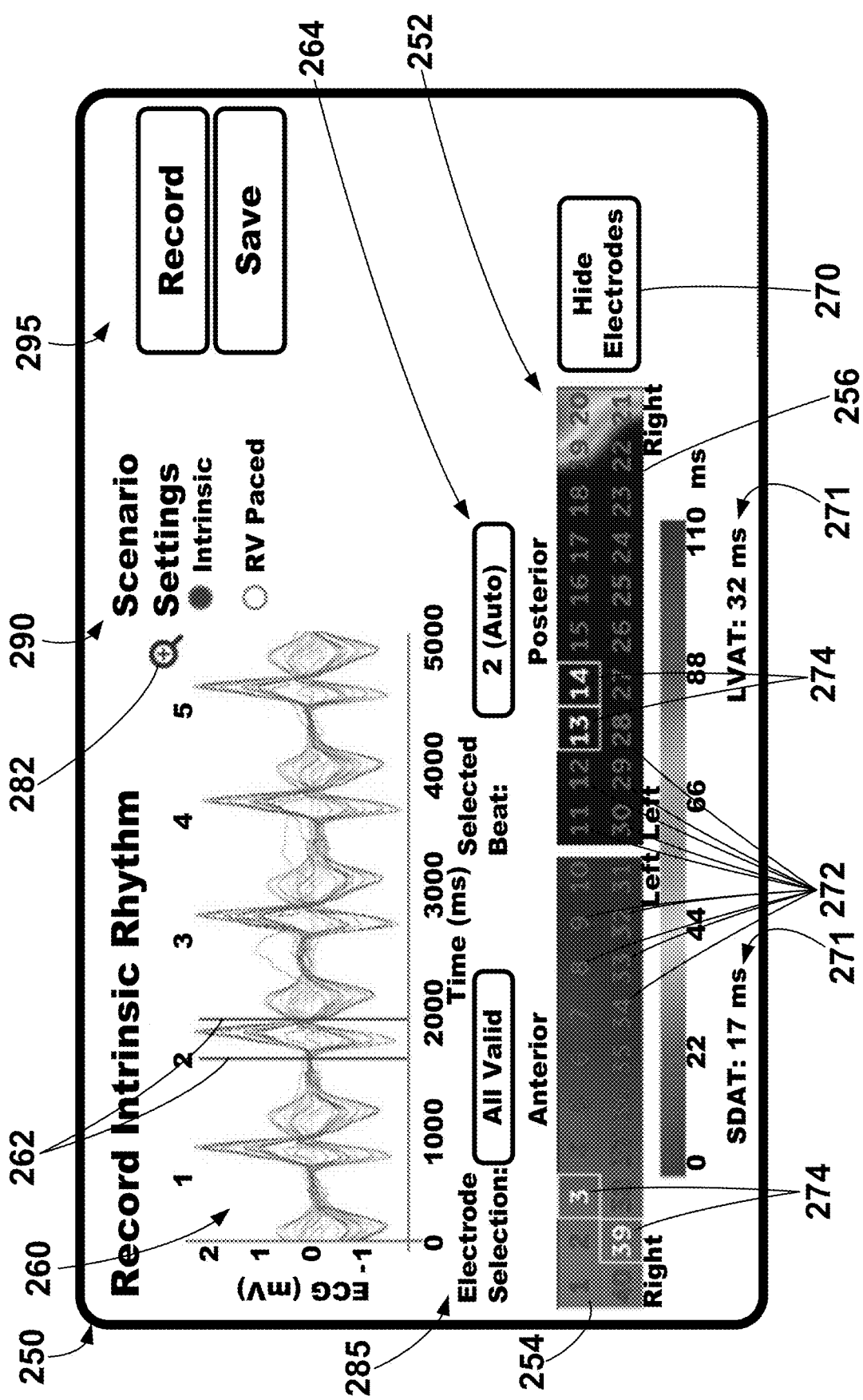
Figure 5C:
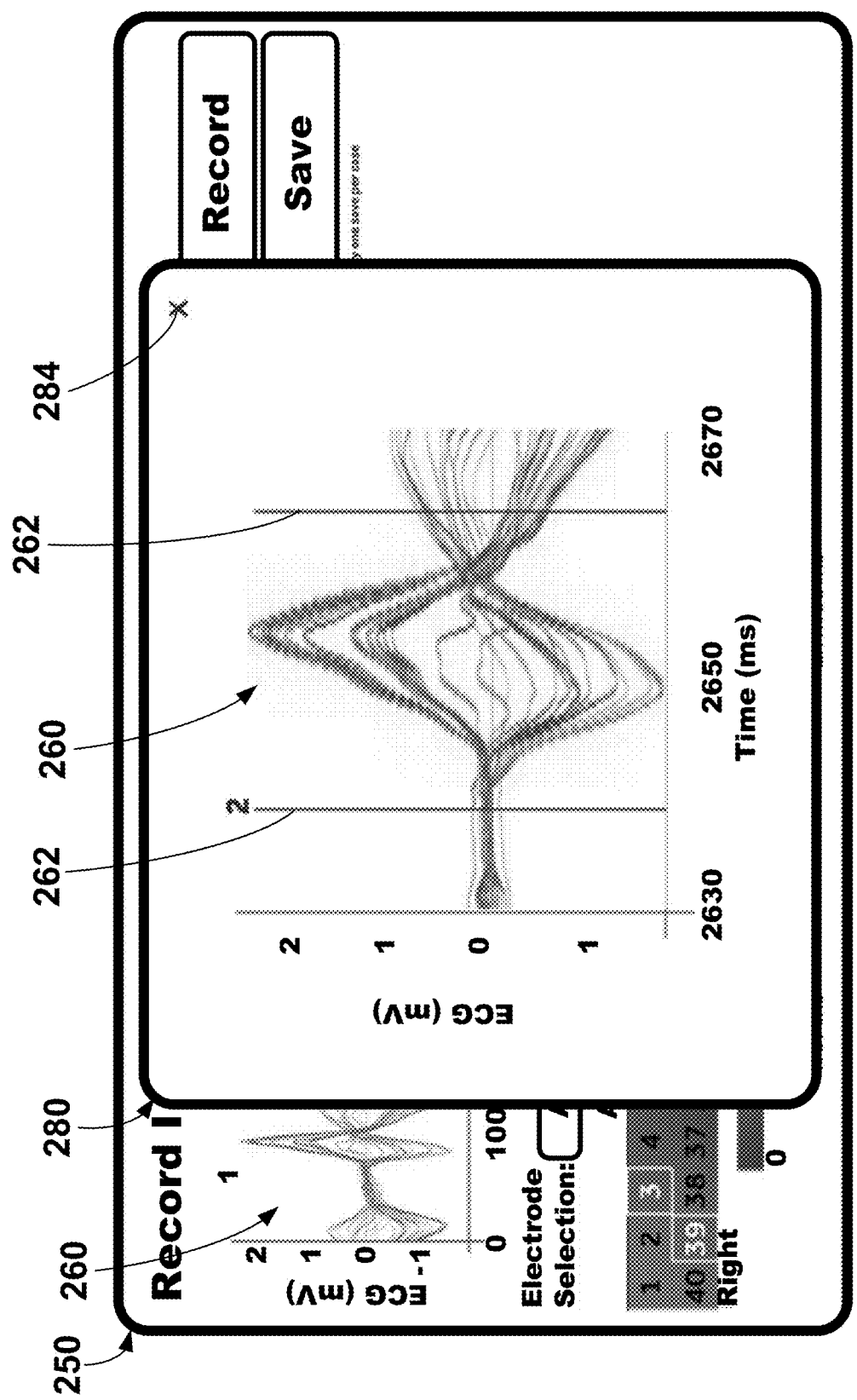
FIG. 5C is the graphical user interface of FIG. 5B including an enlarged graphical region depicting a single cardiac cycle.

Illustrative graphical user interfaces 250 depicting, among other things, a graphical map of electrical activation 252 are shown in FIGS. 5A-5C. In one or more embodiments, the graphical map of electrical activation 252 may be a color-coded, or gray-scaled, two-dimensional map representing the electrical activation about a portion of the surface of a patient's torso. In the example depict in FIGS. 5A-5C, the graphical map of electrical activation 252 includes an anterior area 254 depicting the activation times measured about the anterior torso of the patient and a posterior area 256 depicting the activation times measured about the posterior torso of the patient.

The electrical activation data depicted on the graphical map of electrical activation 252 may be referred to as surrogate electrical activation data (e.g., surrogate electrical activation times, surrogate electrical activation time maps, etc.) and may be defined as data representative of actual, or local, electrical activation data of one or more regions of the patient's heart. For example, electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart.

The graphical map of electrical activation 252 may be further described as extending from a left portion corresponding to anterior side of the patient to a middle portion corresponding to the left side of the patient to a right portion corresponding to the posterior side of the patient. The right side of the anterior area 254 may correspond to the left anterior region of the torso of the patient, and the left side of the anterior area 254 may correspond to the right anterior region of the torso of the patient. Thus, the electrical signal data such as electrical activation measured from the right anterior region of the torso of the patient (e.g., using electrodes positioned on the right anterior region of the torso of the patient) may be depicted on left side of the anterior area 254, and the electrical signal data such as electrical activation measured from the left anterior region of the torso of the patient (e.g., using electrodes positioned on the left anterior region of the torso of the patient) may be depicted on right side of the anterior area 254.

The right side of the posterior area 256 may correspond to the right posterior region of the torso of the patient, and the left side of the posterior area 256 may correspond to the left posterior region of the torso of the patient. Thus, the electrical signal data such as electrical activation measured from the right posterior region of the torso of the patient (e.g., using electrodes positioned on the right posterior region of the torso of the patient) may be depicted on right side of the posterior area 256, and the electrical signal data such as electrical activation measured from the left posterior region of the torso of the patient (e.g., using electrodes positioned on the left posterior region of the torso of the patient) may be depicted on left side of the posterior area 256.

The graphical map of electrical activation 252 may further include an electrical activation key 259 for use in interpreting, or decoding, the anterior and posterior areas 254, 256 of electrical activation. As shown, the electrical activation key 259 may be a color-coded, or gray-scaled, in the same way as the anterior and posterior areas 254, 256.

Further, the graphical user interfaces 250 may include, or depict, a plurality of electrode signals 260 over a plurality of cardiac cycles. More specifically, as shown, the plurality of electrode signals 260 may be described as being graphed, or plotted, over time where the y-axis represents voltage of the electrode signals 260 and the x-axis represents time in milliseconds. The electrode signals 260 may be plotted for a plurality of cardiac cycles (e.g., continuous cardiac cycles), each of which may be numerically labeled. As shown, five cardiac cycles number one through 5 are depicted. Additionally, the cardiac cycles may be plotted over a selected time period regardless of how many cardiac cycles occur within the selected time period. In one embodiment, the selected time period may be five seconds.

A cardiac cycle, or beat, may be selected, and the selected cardiac cycle may be indicated as being selected within the plurality of electrodes signals 260 over the plurality of cardiac cycles. In this example, the selected cardiac cycle is indicated by being bounded by a pair of solid vertical lines 262 (e.g., shown between red calipers). In one or more embodiments the solid vertical lines 262 may represent or correspond to the onset and offset of the selected cardiac cycle (e.g., QRS onset/offset). The cardiac cycle may be automatically selected by the illustrative systems and process described herein, e.g., selected to be the best representation of useful data. As shown, cardiac cycle "2" has been automatically selected as indicated by the word "Auto" in the cardiac cycle selection region 264. In one or more embodiments, the cardiac cycle that is determined to be most typical, or more representative, of the patient's cardiac health or status may be selected. Automatic cardiac cycle selection may be described in U.S. Provisional Patent Application. Ser. No. 62/538,337 filed on Jul. 28, 2017, and entitled "Cardiac Cycle Selection," which is herein incorporated by reference in its entirety.

The cardiac cycle selection region 264 may be further used by a user to select one of the cardiac cycles of plurality of electrode signals 260. For example, a user may select (e.g., click, touch, etc.) the cardiac cycle selection region 264, which may then display a dialog include the remaining cardiac cycles that may be selectable by a user. If a new cardiac cycle is selected, the new cardiac cycle may be indicated as being selected within the cardiac cycle selection region 264 in the same way as the previously selected cardiac cycle (e.g., bounded by a pair of solid vertical lines). It is to be understood that this embodiment is one example of cardiac cycle selection and indication and that other graphical dialogs, regions, and areas may be used to select a cardiac cycle. For example, in one embodiment, a user may select a cardiac cycle by selecting (e.g., click, touch, etc.) the cardiac cycle, or the numerical identifier corresponding thereto, on the graphical representation of the plurality of electrode signals 260 on the graphical user interface 250. In other words, a user may directly select cardiac cycle on the graph depicting the cardiac cycles.

The graphical map of electrical activation 252 corresponds to the electrical activation of the selected cardiac cycle. Thus, in this example, the graphical map of electrical activation 252 corresponds to the electrical activation of cardiac cycle "2." If another cardiac cycle were selected by a user using the cardiac cycle selection region 264 or automatically by the systems and methods described herein, the graphical map of electrical activation 252 depicted on the graphical user interface 250 will change so as to correspond to the electrical activation of the newly selected cardiac cycle. In other words, the graphical map of electrical activation 252 may be displayed based on the monitored electrical activity for the selected cardiac cycle.

As shown in FIG. 5B, the graphical user interface 250 may be further configured to display a plurality of electrode elements 272 corresponding to and positioned on the graphical map of electrical activation 252 in relation to the physical location of the plurality of electrodes located proximate the patient's skin (which, e.g., are used to capture electrical activation data displayed on the graphical map 252). As shown in this example, the plurality of electrode elements 272 are alphanumeric characters (e.g., numbers) identifying the electrodes. The electrodes attached, or coupled, to the patient may also be numbered, which may correspond to the electrode elements 272.

The electrode elements 272 may be displayed by a user selecting an electrode element display region 270 of the graphical user interface 250 as shown in FIG. 5A. When the electrode elements 272 are displayed as shown in FIG. 5B, the electrode element display region 270 may be selected to hide the electrode elements 272 (e.g., return to the interface 250 of FIG. 5A). In other words, the exemplary systems, methods, and interfaces may allow a user to hide or display the plurality of electrode elements 272 using, e.g., the electrode element display region 270.

Additionally, which of the plurality of electrode elements 272 corresponds to electrodes that are ineffective in providing a valid sensing signal from the tissue of the patient may be graphically indicated within the graphical map of electrical activation 252. In the example depicted in FIG. 5B, the ineffective electrode elements 274 that correspond to ineffective electrodes are a different color from the electrode elements 272 that are effective. Further, the electrode elements 274 that correspond to ineffective electrodes are encircled by a box. In this way, a user may be able to quickly identify which of the plurality of electrodes are ineffective and effective, and where within the graphical map of electrical activation 252 such electrode effective or ineffective electrode signals are derived from. As shown, electrodes 3, 13, 14, and 39 are indicated as being ineffective, which corresponds to the interface 200 of FIG. 4 where electrodes 13 and 39 were not in contact and electrodes 3 and 14 had poor signal.

Further, when electrodes, and therefore, the electrode signals derived therefrom are determined to be ineffective, the exemplary systems, methods, and interfaces described herein may be configured to interpolate the electrical activation of each area of the graphical map 252 of electrical activation corresponding to such ineffective external electrodes. Thus, when used in conjunction with the depiction of ineffective electrode elements 274, a user may ascertain that the electrical activation depiction on the graphical map 252 corresponding to ineffective electrode elements 274 may not be based on actual, measured electrical activation at that location, and instead, may be based on interpolated data from effective electrode signals proximate to the ineffective electrodes.

More specifically, the activation maps may be created by interpolating a 2-by-20 matrix of activation times by first using an inverse distance-weighted interpolation step followed by a two-dimensional bi-cubic interpolation method. Further, for each electrode (e.g., iterated over all electrodes), (a) if an electrode is marked as valid, the activation time is directly used in the bi-cubic interpolation step or (b) if an electrode is marked as invalid, find all valid electrodes within the same belt plane (anterior or posterior). The contribution of each valid electrode to the interpolation is its activation time value may be weighted by the inverse of the distance squared from the invalid electrode using the following:

$$AT_{invalid} = \sum_{k=1}^{N} \frac{\left(\frac{1}{dist_k}\right)^2 \times AT_{k,valid}}{\left(\frac{1}{dist_k}\right)^2}$$

Where $$dist_k = \sqrt{(x_{invalid} - x_{k,valid})^2 + (y_{invalid} - y_{k,valid})^2}$$

Next, using the 2×20 array of activation times, for each set of 2×2 neighboring points that form a 'unit square', a system of 16 equations may be solved to find 16 coefficients of a two-dimensional polynomial function that can find the interpolated value at any fractional part within the unit square. Then, such processes may be repeated for all possible neighboring 2×2 point sets.

In one or more embodiments, one or more areas of conduction block may be depicted on the graphical map of electrical activation 252 based on the monitored electrical activity for the selected cardiac cycle. For example, the conduction block may be indicated by a thick colored line on the graphical map of electrical activation 252. In other embodiments, the conduction block may be represented by a "break" in the graphical map of electrical activation 252. For example, different portions or areas of the graphical map of electrical activation 252 may be split off from one another such that a space or gap exists between the split off portions or areas.

The graphical user interface 250 may further display at least one metric of electrical heterogeneity 271 based on the monitored electrical activity for the selected cardiac cycle. As shown, the metrics of electrical heterogeneity 271 depicted are SDAT and LVAT. The SDAT may be defined as the global standard deviation of surrogate electrical activation times monitored by a plurality of external electrodes. The LVAT may be defined as an average of electrical activation times monitored by two or more left external electrodes (e.g., two or more left external electrodes configured to be located proximate the left side of the patient).

A user may desire to more closely view the selected cardiac cycle of the plurality of electrode signals 262. Thus, the interface 250 may be further configured to depict an enlarged graphical region 280 depicting a single cardiac cycle. Similar to as shown in FIGS. 5A-5B the enlarged graphical region 280 depicts the plurality of electrode signals 260 and a pair of solid vertical lines 262 bounding, or identifying, the selected cardiac cycle, which in this example is cardiac cycle "2." Further, in one or more embodiments the solid vertical lines 262 may represent or correspond to the onset and offset of the selected cardiac cycle (e.g., QRS onset/offset). To display the enlarged graphical region 280, a user may select the magnifying glass graphical element 282 as depicted in FIGS. 5A-5B. To minimize, or close, the enlarged graphical region 280, a user may select the close graphical element 284 of the enlarged graphical region 280 depict in FIG. 5C, which will return the user to the interface as provided in FIGS. 5A-5B.

The graphical user interface 250 may be further configured to depict measured electrical activity for a plurality of different cardiac therapy scenarios including no cardiac therapy delivered or intrinsic activation. For example, as shown in FIGS. 5A-5B, the graphical user interface 250 is depicting intrinsic cardiac electrical activation of the patient. In other words, no cardiac therapy was delivered to the patient when the electrical signal data that is currently being displayed was monitored or measured from the patient. The graphical user interface 250 may include a cardiac therapy scenario graphical region 290, which may be useable by a user to select none or one or more various cardiac therapy scenarios. For each different selected cardiac therapy scenario, the graphical user interface 250 may display the plurality of electrode signals 260 over a plurality of cardiac cycles corresponding to the selected cardiac therapy scenario, and the graphical map of electrical activation 252 will correspond to the selected cardiac cycle of the plurality of electrode signals 260 of, or corresponding to, the selected cardiac therapy scenario.

For example, in FIGS. 5A-5B, the selected cardiac therapy scenario is "intrinsic" where no cardiac therapy (e.g., no cardiac resynchronization therapy) is being delivered to the patient, and thus, the plurality of electrode signals 260 and the graphical map of electrical activation 252 are based on electrical activity measured, or monitored, without the delivery of cardiac therapy (e.g., based on intrinsic activation). However, a user may select a different cardiac therapy scenario using the cardiac therapy scenario graphical region 290. For example, as shown in FIGS. 5A-5B, a user may select a RV-paced cardiac therapy scenario (e.g., also where no cardiac resynchronization therapy is being delivered).

Figure 6:
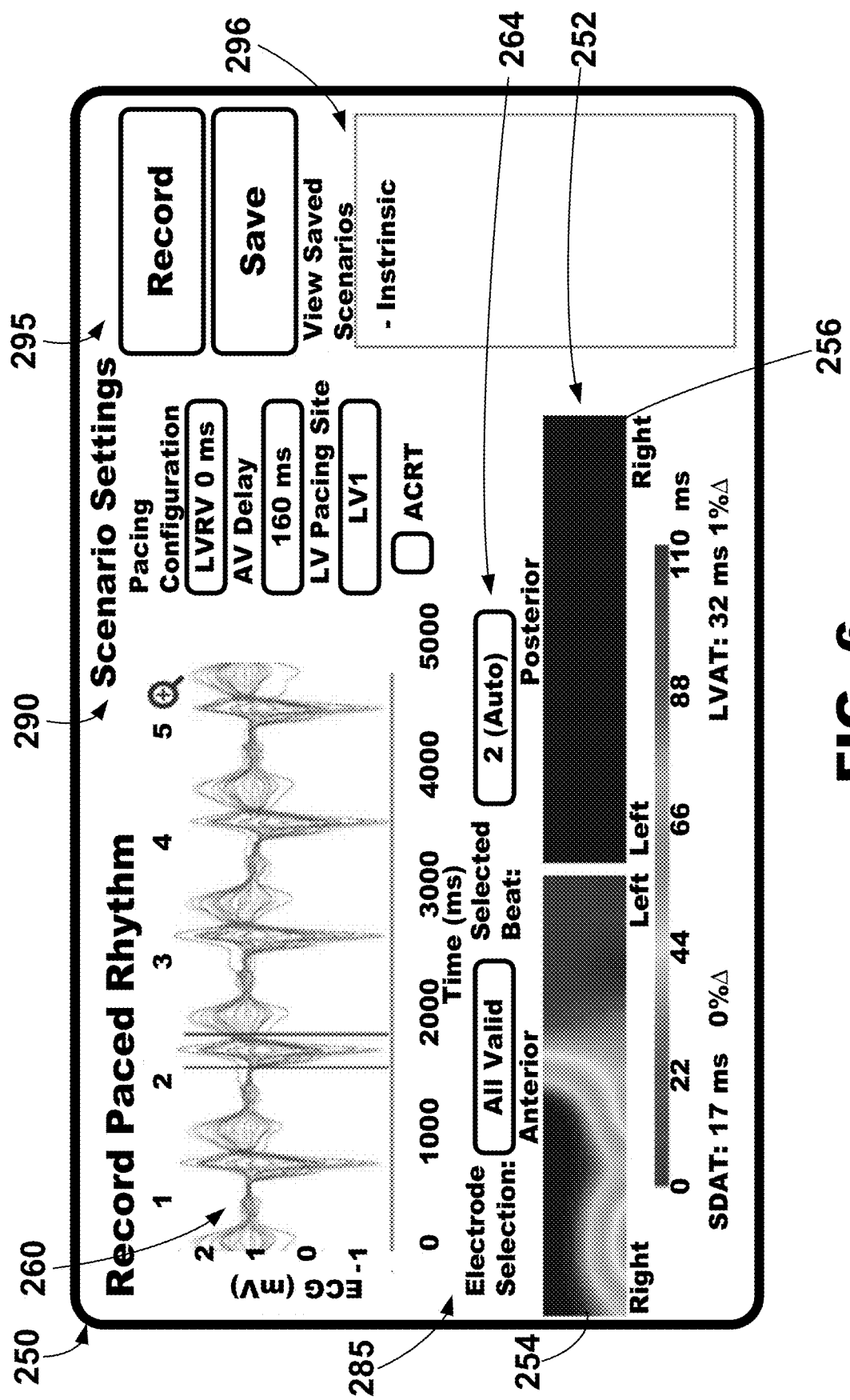
FIG. 6 is an illustrative graphical user interface depicting, among other things, a graphical map of electrical activation and cardiac therapy scenario graphical, e.g., for use with the systems and external electrode apparatus of FIGS. 1-3.

An illustrative graphical user interface 250 depicting, among other things, a plurality of electrode signals 260, a graphical map of electrical activation 252, and a cardiac therapy scenario selection region 290 where cardiac therapy has been selected is depicted in FIG. 6. As shown, a cardiac therapy scenario has been selected in this embodiment, and more specifically, cardiac therapy has been selected where the LV-RV, or V-V, delay is 0 milliseconds (ms), the A-V delay is 160 ms, and the pacing site is LV1 (e.g., a particular electrode of a lead). Thus, the plurality of electrode signals 260 and the graphical map of electrical activation 252 correspond to the electrical data measured, or monitored, from a patient during the selected cardiac therapy scenario, which as described in this example is cardiac therapy that utilizes a V-V delay of 0 ms, an A-V delay of 120 ms, and the LV1 pacing site.

As shown in FIG. 6, the cardiac therapy scenario selection region 290 may include a plurality of various cardiac therapy settings. In this example, the plurality of various cardiac therapy settings include at least one of pacing configuration (e.g., RV-LV, LV-RV, LV only, RV only, etc.), V-V delay, A-V delay, LV pacing site, and adaptive cardiac resynchronization therapy (ACRT). In other examples, the plurality of various cardiac therapy settings may include one or more of multipoint pacing, LV-LV delay, etc.

In some embodiments, when a cardiac therapy scenario is changed or modified by a user, the delivered cardiac therapy may be changed in real time, and the monitored electrical activity upon which the electrical data depicted in the graphical user interface 250 may be updated in real time. In other words, the systems, methods, and interfaces described herein may provide adjustment of cardiac therapy and real-time feedback from such adjustment of cardiac therapy.

In other embodiments, the electrical data may be measured and recorded for each of the plurality of different cardiac therapy scenarios, and when a user selects a cardiac therapy scenario, the electrical data depicted in the graphical user interface 250 may be updated based on the data measured and recorded previously using the selected cardiac therapy scenario. In other words, the systems, methods, and interfaces described herein may provide evaluation of a plurality of different cardiac therapy scenarios after such data for such different cardiac therapy scenarios has been monitored and recorded.

Additionally, the illustrative systems, methods, and interfaces may be a hybrid of both systems where the data for a cardiac therapy scenario may be monitored and displayed in real time while the cardiac therapy is being adjusted, and then optionally recorded and saved for later viewing. For example, the graphical user interface 250 may include a record and save graphical elements 295 that may be used to record and save monitored electrical activity for a particular cardiac therapy scenario and a view saved scenario graphical region 296 that may be used to select previously recorded and saved electrical activation data for a particular cardiac therapy scenario. In particular, the record graphical element may initiate the recording of a patient's electrical activation using the external electrode apparatus over a selected time period such as five seconds, and the save graphical element may allow such recorded data to be saved for use in further analysis. As shown, the view saved scenario graphical region 296 includes one cardiac therapy scenario: namely, intrinsic. Selection of the intrinsic cardiac therapy scenario may depict, or display, the electrical activation data of FIGS. 5A-5B.

As noted herein, the cardiac cycle (e.g., from which the graphical map of electrical activation 252 and metrics of electrical heterogeneity 271 are derived from) may be automatically selected by the illustrative systems and methods. In one embodiment, selecting one cardiac cycle of the plurality of cardiac cycles may include selecting the cardiac cycle of the plurality of cardiac cycles having characteristics (e.g., median, minimum, maximum, and/or summed signal amplitude characteristics) that represent the patient's typical or representative cardiac cycle.

Additionally, the illustrative graphical user interface 250 may include an electrode selection graphical region 285 that may be used by a user to select an electrode set of a plurality of different electrode sets of the plurality of external electrodes to be used for the measurement of electrical data for display on the graphical user interface 250. For example, the plurality of electrode signals 260 over the plurality of cardiac cycles that is displayed may only include electrode signals of the selected electrode set, and the displayed graphical map of electrical activation 252 may be based on the monitored electrical activity from only electrode signals of the selected electrode set. The electrode sets may include all valid signals, which as shown in FIGS. 5A-B & 6 is presently selected, and thus, all electrode signals were used to generate the maps of electrical activation and calculate the metrics of electrical heterogeneity. In other embodiments, the electrode sets may include only anterior signals, only posterior signals, only left anterior signals, only left posterior signals, only a subset of the signals most proximate to the patient's heart, the signal most proximate to the V1 location of a standard 12-lead ECG, the signals covering the same area but not the same pattern, etc.

Figure 7:
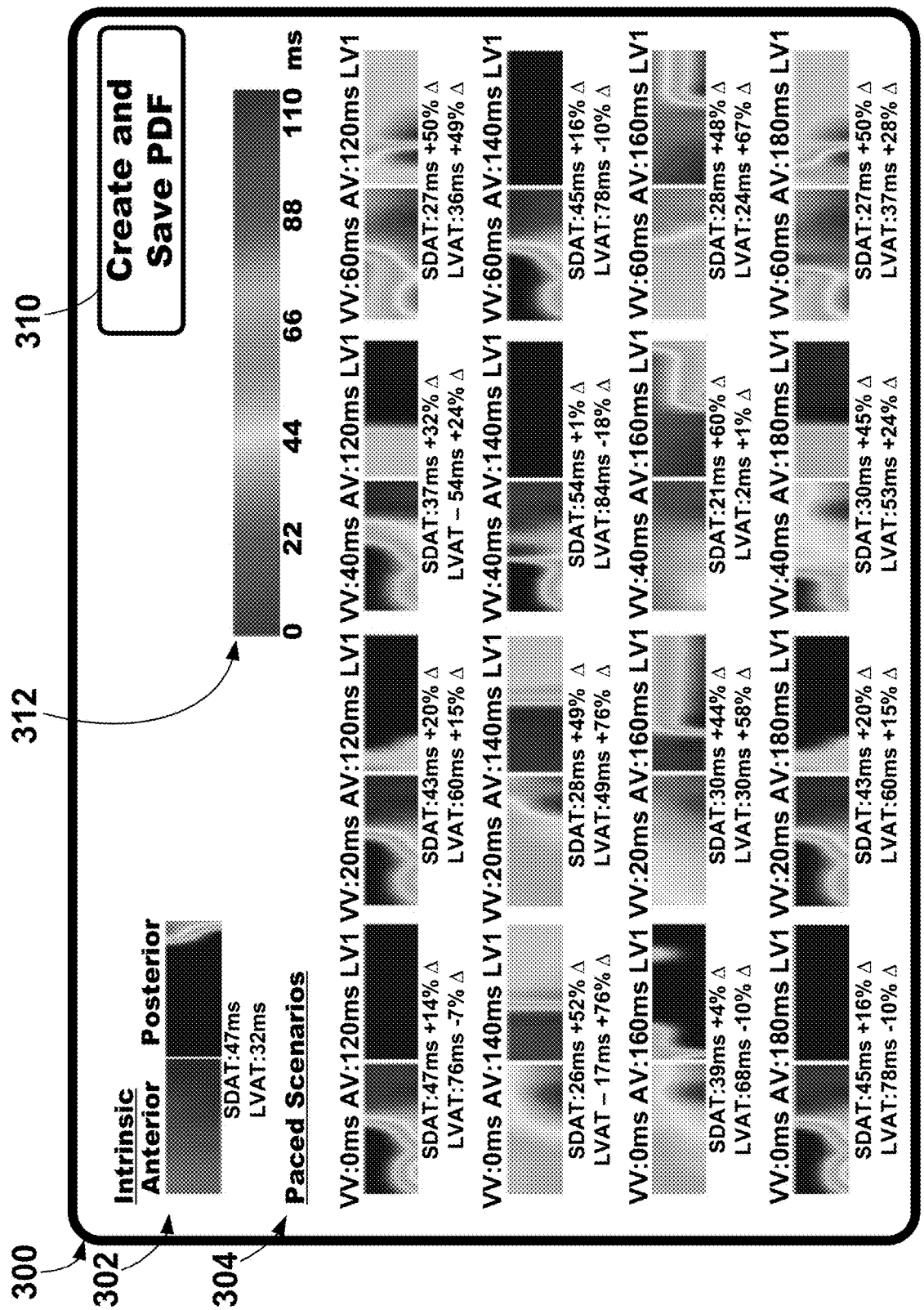
FIG. 7 is an illustrative graphical user interface depicting, among other things, a plurality of graphical maps of electrical activation corresponding to different cardiac therapy scenarios, e.g., for use with the systems and external electrode apparatus of FIGS. 1-3.

An illustrative graphical user interface 300 depicting, among other things, a plurality of graphical maps of electrical activation from external electrodes corresponding to different cardiac therapy scenarios is depicted in FIG. 7. Each of the plurality of graphical maps of electrical activation may correspond to a different cardiac therapy scenario of the plurality of different cardiac therapy scenarios than each other. Each of the graphical maps of the electrical activation of graphical user interface 300 may be similar to the graphical maps of electrical activation as described herein with respect to FIGS. 5A-5B & 6. For example, each of the graphical maps of the electrical activation of the graphical user interface 300 may include an anterior area depicting the activation times measured about the anterior torso of the patient and a posterior area depicting the activation times measured about the posterior torso of the patient, and may extend from the right anterior to the left anterior to the left side to the left posterior to the right posterior. Further, the graphical user interface 300 may include a plurality of metrics of electrical heterogeneity corresponding to the plurality of graphical maps of electrical activation. In this example, two metrics of electrical heterogeneity are displayed proximate and corresponding to each of the plurality of graphical maps of electrical activation.

More specifically, SDAT and LVAT are displayed proximate and corresponding to each of the plurality of graphical maps of electrical activation. Additionally, a percentage change of each of the metrics of electrical heterogeneity are displayed, or depicted, proximate the metrics. The percentage change may be the percentage change from the metrics of electrical heterogeneity computed, or determined, from an intrinsic cardiac therapy scenario (where no cardiac resynchronization therapy is delivered). In other embodiments, the percentage change may be the percentage change from the metrics of electrical heterogeneity computed, or determined, from a baseline cardiac therapy scenario (e.g., the cardiac therapy that may be delivered to a patient prior to the present evaluation).

As shown, the graphical user interface 300 may include a graphical map of intrinsic electrical activation 302 and a plurality of graphical maps of paced electrical activation 304, each having a different cardiac therapy scenario associated therewith. Additionally, each of the plurality of graphical maps of paced electrical activation 304 may be arranged in accordance with the adjustment of the cardiac therapy settings. For example, when moving from left to right (e.g., from column to column) and when moving from top to bottom (e.g., from row to row) one or more cardiac therapy settings may be adjusted or changed. In this way, a user may be able to view the graphical user interface 300 and ascertain which of the plurality of different cardiac therapy scenarios may be beneficial (e.g., most beneficial) or effective for the patient.

In this illustrative embodiment, the first column may represent cardiac therapy scenarios having a V-V delay of 0 ms, the second column may represent cardiac therapy scenarios having a V-V delay of 20 ms, the third column may represent cardiac therapy scenarios having a V-V delay of 40 ms, and the fourth column may represent cardiac therapy scenarios having a V-V delay of 60 ms. Further, the first row may represent cardiac therapy scenarios having a A-V delay of 120 ms, the second row may represent cardiac therapy scenarios having a A-V delay of 140 ms, the third row may represent cardiac therapy scenarios having a A-V delay of 160 ms, and the fourth row may represent cardiac therapy scenarios having a A-V delay of 180 ms. It is to be understood that the A-V and V-V delays used and shown in the column and rows of FIG. 7 is one example, and the disclosure herein contemplates other A-V and V-V delays. For example, A-V delays ranging from about 80 ms to about 240 ms at steps of 20 ms and V-V delays ranging from about 0 ms to about 80 ms at steps of 20 ms may be utilized. Additionally, the plurality of graphical maps of paced electrical activation 304 could be organized, or arranged, by LV pacing site or LV pacing vector (in the example depicted, the pacing site is always LV1).

Further, it may be described that the organization could be primarily dictated by V-V delay, secondarily by A-V delay, and tertiarily by LV pacing site or in a any other different order of priority. Also, a clinician could be provided a choice of different filtering options.

Still further, the graphical user interface 300 may include an electrical activation key 312 for use in interpreting, or decoding, the graphical maps of electrical activation. As shown, the electrical activation key 312 may be a color-coded, or gray-scaled, in the same way as the anterior and posterior areas of the graphical maps of electrical activation. Still further, the graphical user interface 300 may include a create and save graphical region 310 configured for selection by a user to create and save a digital file of the data depicted, or shown, on the graphical user interface 300. In one example, the create and save graphical region 310 may be used to generate a portable, printable digital file that may be viewed consistently on many different types of computers and printed consistently on many different types of printers.

The illustrative systems, methods, and interface described herein may be configured to evaluate and sort a plurality of different cardiac therapy scenarios based on the monitored electrical activation which was obtained for each of different cardiac therapy scenarios. One or more metrics of electrical heterogeneity, or electrical dyssynchrony, may be used by the evaluation and sorting of the cardiac therapy scenarios.

Figure 8A:
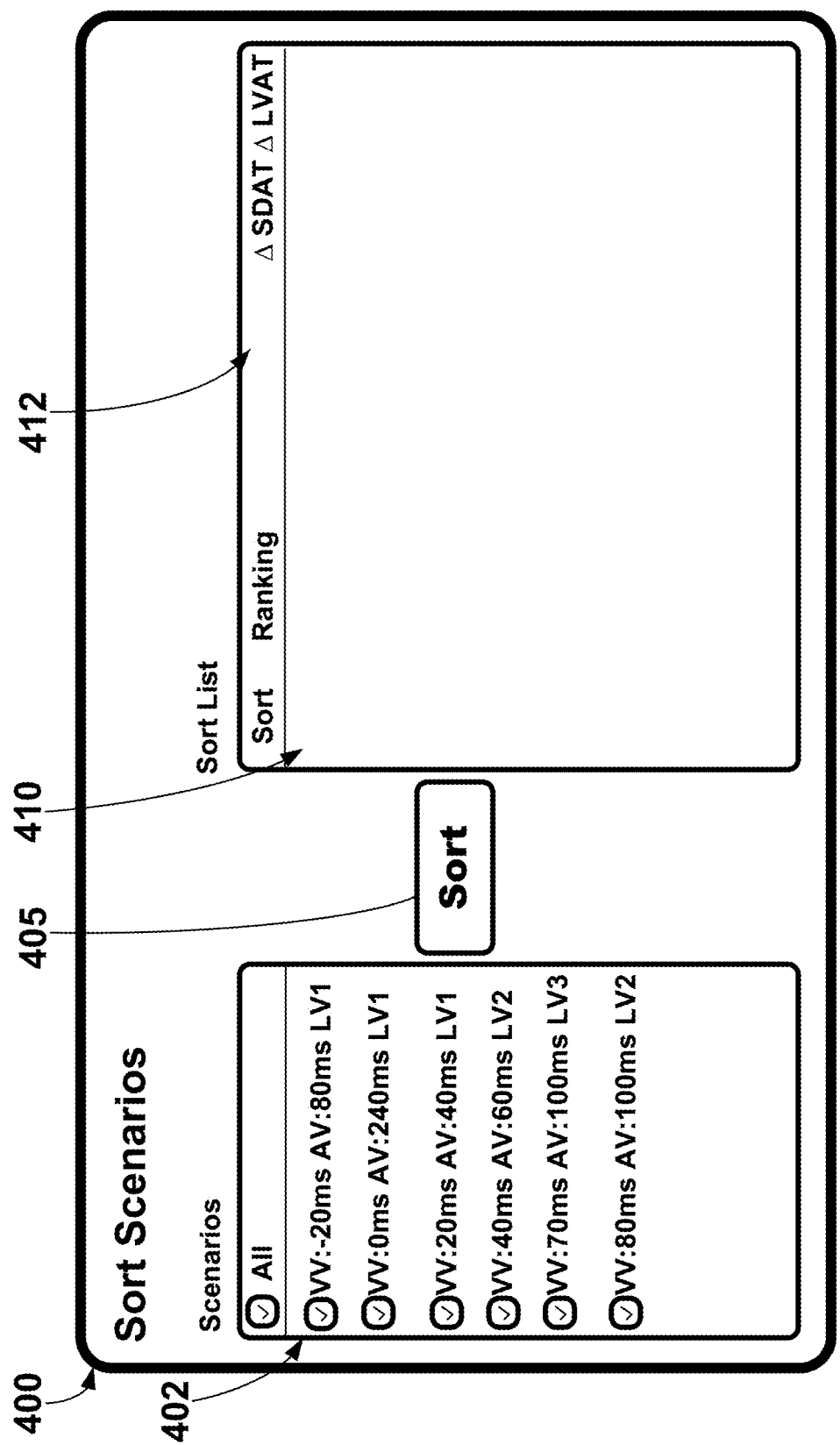
FIG. 8A is an illustrative graphical user interface for evaluation and sorting of cardiac therapy scenarios including a cardiac therapy scenario selection region, e.g., for use with the systems and external electrode apparatus of FIGS. 1-3.
Figure 8B:
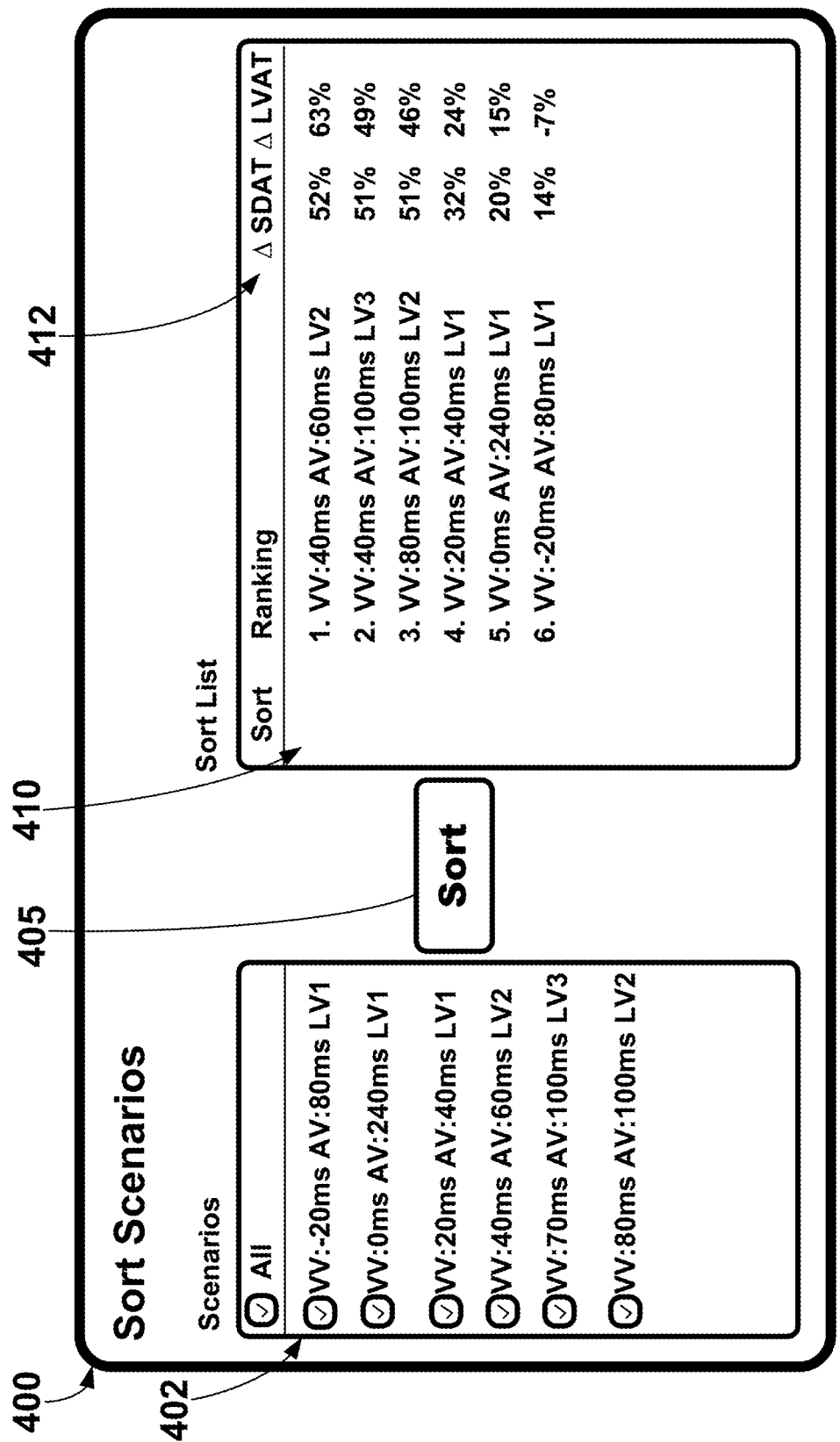
FIG. 8B is an illustrative graphical user interface depicting a ranking of selected cardiac therapy scenarios from the cardiac therapy scenario selection region of FIG. 8A, e.g., for use with the systems and external electrode apparatus of FIGS. 1-3.
Figure 8C:
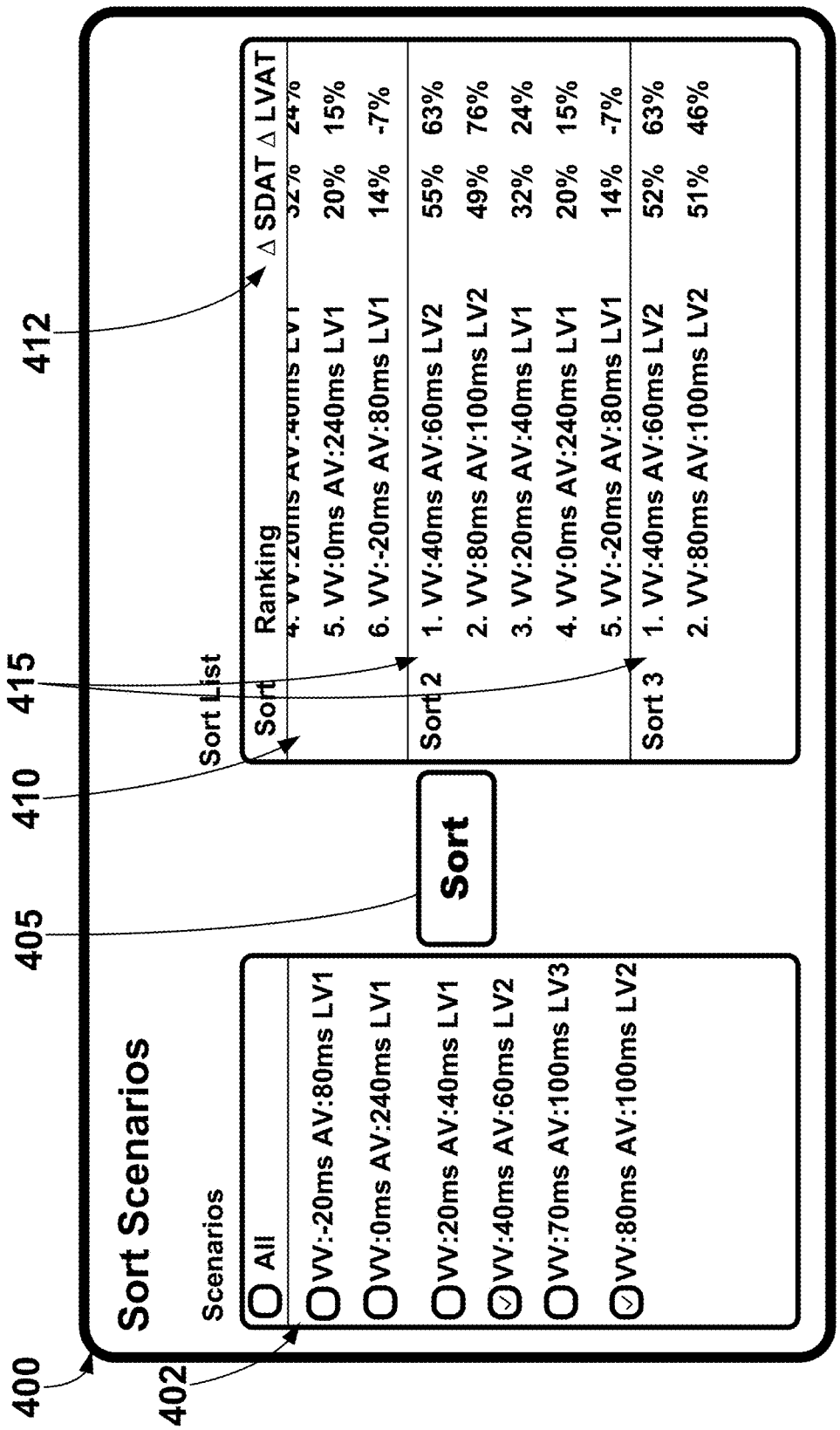
FIG. 8C is another illustrative graphical user interface depicting more rankings of selected cardiac therapy scenarios, e.g., for use with the systems and external electrode apparatus of FIGS. 1-3.

One illustrative evaluation and sorting graphical user interface 400 is depicted in FIGS. 8A-8C. The graphical user interface 400 of FIG. 8A depicts a cardiac therapy scenario selection region 402. The cardiac therapy scenario selection region 402 may be configured to allow a user to select one or more cardiac therapy scenarios that the illustrative systems, methods, and interfaces may evaluate and sort. As shown, all of the available cardiac therapy scenarios (where electrical activation data have been monitored, or collected, for use in cardiac therapy evaluation) are presently selected as indicated by the checkmarks besides each of the cardiac therapy scenarios. A user may select or deselect (e.g., clicking, touching, etc.) each of the cardiac therapy scenarios using the cardiac therapy scenario selection region 402, and after a user has selected the cardiac therapy scenarios, the user may select the sort initiation region 405.

Selection of the sort initiation region 405 may initiate, or execute, the initial sorting of the cardiac therapy scenarios as shown in FIG. 8B. The illustrative graphical user interface 400 of FIG. 8B depicts a ranking of selected cardiac therapy scenarios that have been sorted, or ranked, based on generated electrical heterogeneity information generated for each of the selected cardiac therapy scenarios within a sort graphical region 410. In one or more embodiments, the selected cardiac therapy scenarios are ranked based on a primary metric of electrical heterogeneity. In this example, the primary metric of electrical heterogeneity may be SDAT. In another embodiment, the primary metric of electrical heterogeneity may be LVAT. These metrics, or other metrics of electrical heterogeneity, 412 for each of the selected cardiac therapy scenarios may also be depicted in the sort graphical region 410 as well as the percentage change from baseline therapy or intrinsic activation.

In the event of a "tie," the selected cardiac therapy scenarios may be further ranked, or sorted, based on a secondary metric of electrical heterogeneity such as, e.g., SDAT or LVAT. In this embodiment, the secondary metric of electrical heterogeneity may be LVAT. In other words, two or more of the selected cardiac therapy scenarios may be further ranked based on a secondary metric of electrical heterogeneity if the primary metric of electrical heterogeneity of the two more selected cardiac therapy scenarios are within a selected threshold, or range, (e.g., 5%) from each other. In other words, for example, the ranked order may be accomplished through the following steps using the SDAT and LVAT values for the selected pacing scenarios: rank the pacing scenarios in order of smallest to largest SDAT percent change values, assign a rank of 1 to all pacing scenarios within 3% of the smallest SDAT, and for all pacing scenarios with a ranking of 1, demote any pacing scenario with an LVAT percent change more than 30 percent greater than the minimum LVAT percentage change of the pacing scenarios ranked 1.

Further, the graphical user interface 400 may be further configured to depict multiple sorts, or rankings, within the sort graphical region 410 as shown in FIG. 8C. In particular, a plurality of rankings 415 of the different groups of selected cardiac therapy scenarios may be depicted, or shown, in the sort graphical region 410. The plurality of rankings 415 of the different groups of selected cardiac therapy scenarios may be generated, and then displayed, by a user selecting different cardiac therapy scenarios using the cardiac therapy scenario selection region 402, and then initiating another sort, or ranking, by selecting the sort initiation region 405.

For example, as shown, the "Sort 3" has been generated by a user selecting two different cardiac therapy scenarios, namely, a first cardiac therapy scenario having a V-V timing of 40 ms, A-V timing of 60 ms, and a LV2 left ventricular pacing location and a second cardiac therapy scenario having a V-V timing of 80 ms, A-V timing of 100 ms, and a LV2 left ventricular pacing location. After selecting the sort initiation region 405, such two cardiac therapy scenarios may be sorted according to a primary metric of electrical heterogeneity (e.g., SDAT), and in this example, the primary metric of electrical heterogeneity of each of the two cardiac therapy scenarios is within 1% of each other, and thus, the secondary metric of electrical heterogeneity (e.g., LVAT) of each of the two cardiac therapy scenarios may be used to completed the sorting or ranking.

Figure 9:
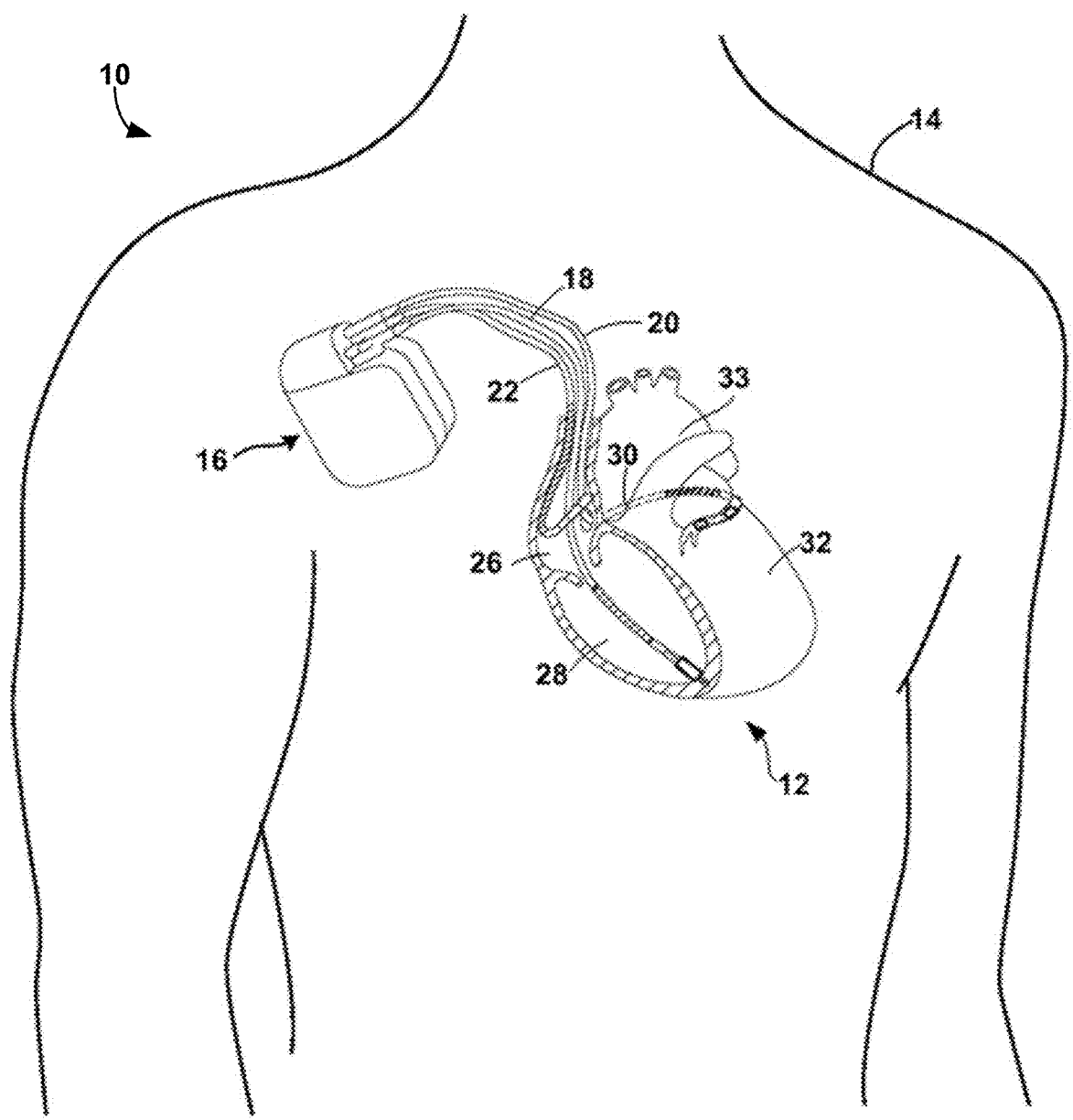
FIG. 9 is a diagram of an exemplary system including an exemplary implantable medical device (IMD).

Exemplary cardiac therapy may be further described herein with reference to FIGS. 9-11. Additionally, the exemplary systems and methods described herein may further use or incorporated the systems and methods described in U.S. Pat. App. Pub. No. 2016/0045737 to Ghosh et al. published on Feb. 18, 2016, U.S. Pat. App. Pub. No. 2016/0045738 to Ghosh et al. published on Feb. 18, 2016, U.S. Pat. App. Pub. No. 2016/0045744 to Gillberg et al. published on Feb. 18, 2016, all of which are incorporated herein by reference in their entireties.

The exemplary systems, methods, and graphical user interfaces described herein may be used with respect to the implantation and configuration of an implantable medical device (IMD) and/or one or more leads configured to be located proximate one or more portions of a patient's heart. For example, the exemplary systems, methods, and interfaces may be used in conjunction with an exemplary therapy system 10 described herein with reference to FIGS. 9-11.

FIG. 9 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 9, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse wide, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 10A:
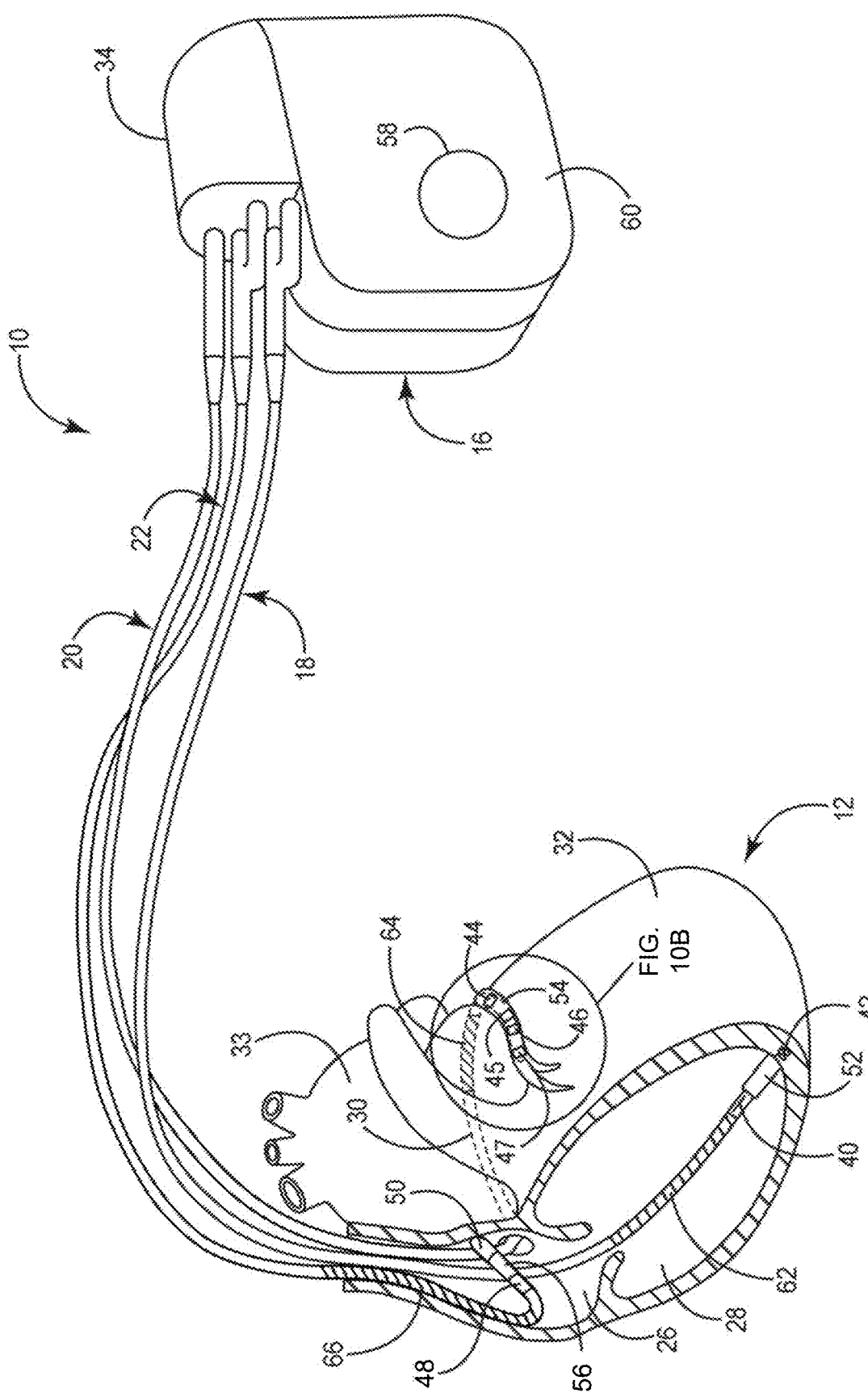
FIG. 10A is a diagram of the exemplary IMD of FIG. 9.
Figure 10B:
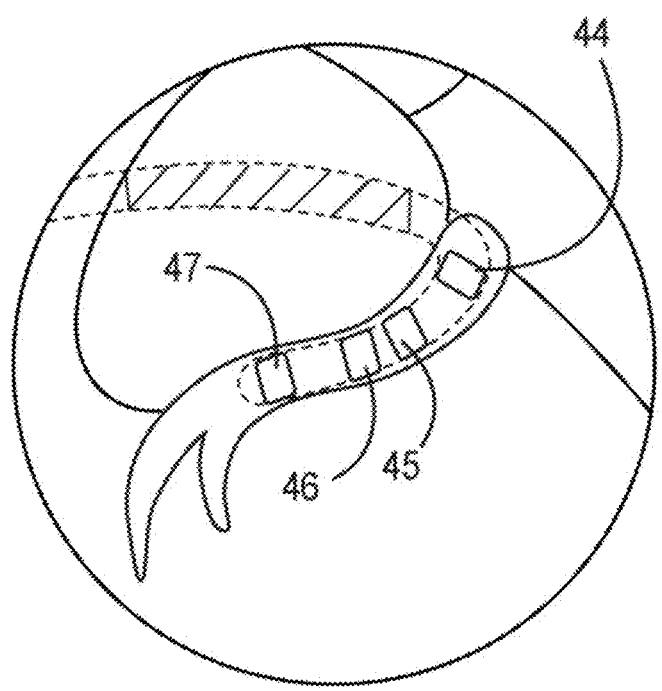
FIG. 10B is a diagram of an enlarged view of a distal end of the electrical lead disposed in the left ventricle of FIG. 10A.

FIGS. 10A-10B are conceptual diagrams illustrating the IMD 16 and the leads 18, 20, 22 of therapy system 10 of FIG. 9 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 $mm^2$ to about 5.8 $mm^2$.

Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 10A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 10A, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the exemplary therapy system 10 illustrated in FIGS. 9-11 is merely one example. In other examples, the therapy system may include epicardial leads and/or patch electrodes instead of or in addition to the transvenous leads 18, 20, 22 illustrated in FIG. 9. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 9). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 9-11. Still further, other therapy systems may include a single lead that extends from the IMD 16 into the right atrium 26 or the right ventricle 28, or two leads that extend into a respective one of the right atrium 26 and the right ventricle 28.

Figure 11A:
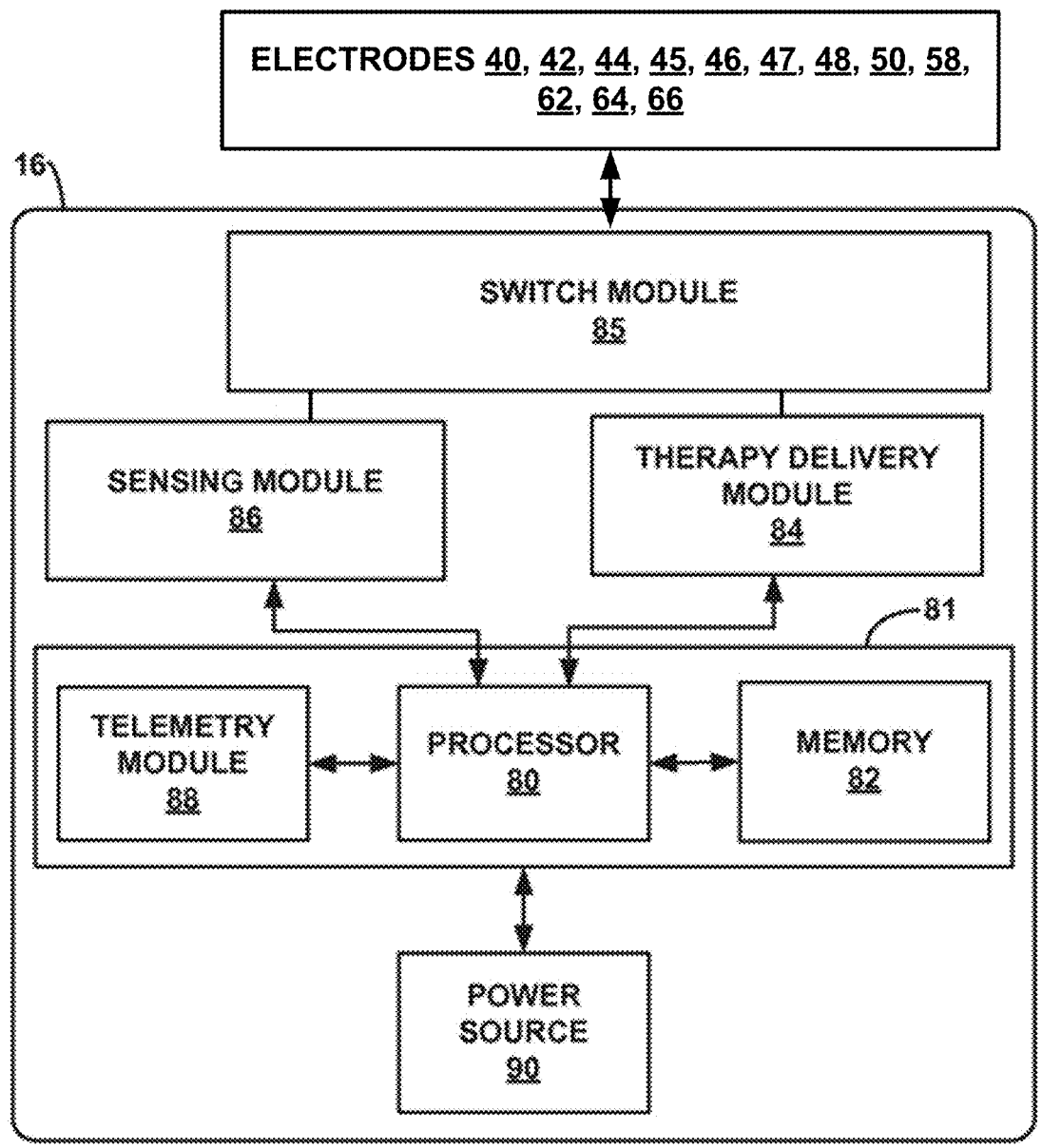
FIG. 11A is a block diagram of an exemplary IMD, e.g., of the systems of FIGS. 9-10.

FIG. 11A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, VV delays, pacing pulses with the amplitudes, pulse widths, frequency, or electrode polarities, etc., which may be specified by one or more selected therapy programs (e.g., AV and/or VV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 11B:
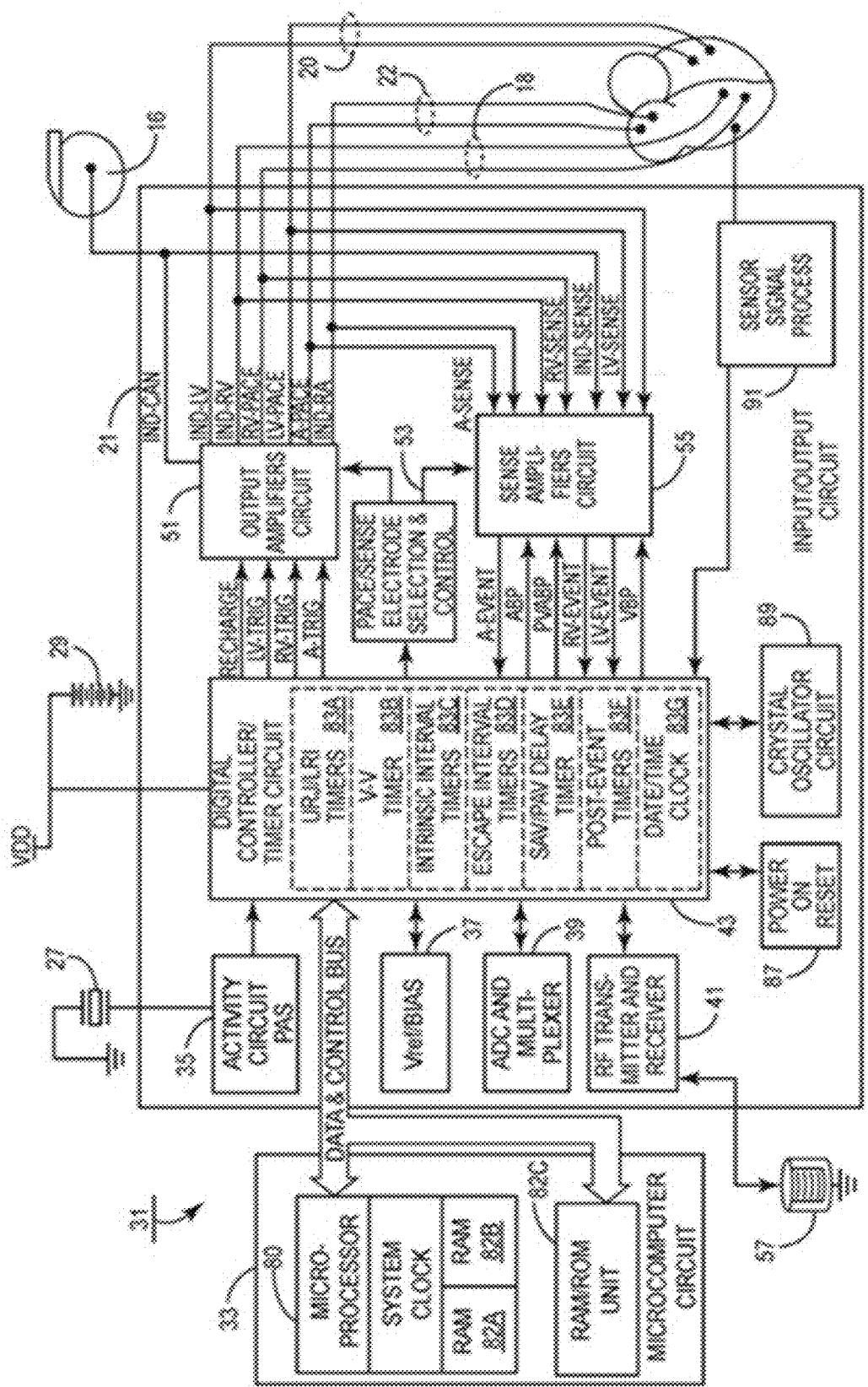
FIG. 11B is another block diagram of an exemplary IMD (e.g., an implantable pulse generator) circuitry and associated leads employed in the systems of FIGS. 9-10.

FIG. 11B is another embodiment of a functional block diagram for IMD 16 that depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in exemplary implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer. The output signal of the patient activity sensor 27 may be processed and used as a RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in its entirety. Similarly, the exemplary systems, apparatus, and methods described herein may be practiced in conjunction with alternate types of sensors such as oxygenation sensors, pressure sensors, pH sensors, and respiration sensors, for use in providing rate responsive pacing capabilities. Alternately, QT time may be used as a rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals, V-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, VV delays, post-ventricular time periods, and post-atrial time periods that vary with the sensor based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by processing circuitry and/or one or more processors to support one or more aspects of the functionality described in this disclosure.

ILLUSTRATIVE EMBODIMENTS

Embodiment 1

A system for use in cardiac evaluation comprising:
electrode apparatus comprising a plurality of external electrodes to be located proximate a patient's skin;
display comprising a graphical user interface to present information for use in assisting a user in at least one of assessing a patient's cardiac health, evaluating and adjusting cardiac therapy delivered to a patient, and navigating at least one implantable electrode to a region of the patient's heart; and
computing apparatus comprising processing circuitry, the computing apparatus operably coupled to the electrode apparatus and the display, the computing apparatus configured to:
monitor electrical activity from the patient's skin using the plurality of external electrodes,
display, on the graphical user interface, a graphical map comprises a plurality of electrode graphical elements corresponding to and positioned on the graphical map in relation to the physical location of the plurality of electrodes located proximate the patient's skin, wherein the graphical map extends from a left portion corresponding to anterior side of the patient to a middle portion corresponding to the left side of the patient to a right side corresponding to the posterior side of the patient, and
display, on the graphical user interface, an effectiveness value proximate each of the plurality of electrode graphical elements representative of the effectiveness of the corresponding electrode in providing a valid sensing signal from the tissue of the patient.

Embodiment 2

A method comprising:
providing a plurality of external electrodes to be located proximate a patient's skin;
monitoring electrical activity from the patient's skin using the plurality of external electrodes;
displaying, on the graphical user interface, a graphical map comprising a plurality of electrode graphical elements corresponding to and positioned on the graphical map in relation to the physical location of the plurality of electrodes located proximate the patient's skin, wherein the graphical map extends from a left portion corresponding to anterior side of the patient to a middle portion corresponding to the left side of the patient to a right side corresponding to the posterior side of the patient; and
displaying, on the graphical user interface, an effectiveness value proximate each of the plurality of electrode graphical elements representative of the effectiveness of the corresponding electrode in providing a valid sensing signal from the tissue of the patient.

Embodiment 3

The embodiment as set forth in any one of embodiments 1-2, wherein the computing apparatus is further configured to execute or the method further comprises displaying, on the graphical user interface, a principal electrodes graphical region proximate one or more electrode graphical elements to indicate which of the plurality of electrodes most significant.

Embodiment 4

The embodiment as set forth in any one of embodiments 1-3, wherein the effectiveness value comprises one of the following three values: good signal (or good contact), poor signal, and not in contact.

Embodiment 5

The embodiment as set forth in any one of embodiments 1-4, wherein the computing apparatus is further configured to execute or the method further comprises displaying, on the graphical user interface, a global electrode connection status message indicative of the state of the plurality of electrodes providing valid sensing signals from the tissue of the patient.

Embodiment 6

A system for use in cardiac evaluation comprising:
electrode apparatus comprising a plurality of external electrodes to be located proximate a patient's skin;
display comprising a graphical user interface to present information for use in assisting a user in at least one of assessing a patient's cardiac health, evaluating and adjusting cardiac therapy delivered to a patient, and navigating at least one implantable electrode to a region of the patient's heart; and
computing apparatus comprising processing circuitry, the computing apparatus operably coupled to the electrode apparatus and the display, the computing apparatus configured to:
monitor electrical activity from the patient's skin using the plurality of external electrodes resulting in a plurality of electrode signals,
display, on the graphical user interface, the plurality of electrode signals over a plurality of cardiac cycles,
select or allow a user to select one cardiac cycle of the plurality of cardiac cycles, and
display, on the graphical user interface, a graphical map of electrical activation based on the monitored electrical activity for the selected cardiac cycle.

Embodiment 7

A method comprising:
providing a plurality of external electrodes to be located proximate a patient's skin;
monitoring electrical activity from the patient's skin using the plurality of external electrodes resulting in a plurality of electrode signals;
displaying, on the graphical user interface, the plurality of electrode signals over a plurality of cardiac cycles;
selecting or allowing a user to select one cardiac cycle of the plurality of cardiac cycles; and
displaying, on the graphical user interface, a graphical map of electrical activation based on the monitored electrical activity for the selected cardiac cycle.

Embodiment 8

The embodiment as set forth in any one of embodiments 6-7, wherein the computing apparatus is further configured to execute or the method further comprises displaying, on the graphical user interface, a plurality of electrode elements corresponding to and positioned on the graphical map of electrical activation in relation to the physical location of the plurality of electrodes located proximate the patient's skin, wherein the graphical map extends from a left portion corresponding to anterior side of the patient to a middle portion corresponding to the left side of the patient to a right side corresponding to the posterior side of the patient.

Embodiment 9

The embodiment as set forth embodiment 8, wherein the computing apparatus is further configured to execute or the method further comprises allowing a user to hide or display the plurality of electrode elements.

Embodiment 10

The embodiment as set forth in any one of embodiments 8-9, wherein the computing apparatus is further configured to execute or the method further comprises graphically indicating, on graphical map of electrical activation, one or more areas of conduction block based on the monitored electrical activity for the selected cardiac cycle.

Embodiment 11

The embodiment as set forth in any one of embodiments 8-10, wherein the computing apparatus is further configured to execute or the method further comprises graphically indicating, on the graphical user interface, which of the plurality of electrode elements corresponds to electrodes that are ineffective in providing a valid sensing signal from the tissue of the patient.

Embodiment 12

The embodiment as set forth in any one of embodiments 6-11, wherein the computing apparatus is further configured to execute or the method further comprises interpolating the electrical activation of each area of the graphical map of electrical activation corresponding corresponds to external electrodes that are ineffective in providing a valid sensing signal from the tissue of the patient.

Embodiment 13

The embodiment as set forth in any one of embodiments 6-12, wherein the computing apparatus is further configured to execute or the method further comprises displaying at least one metric of electrical heterogeneity based on the monitored electrical activity for the selected cardiac cycle.

Embodiment 14

The embodiment as set forth in any one of embodiments 6-13, wherein the computing apparatus is further configured to execute or the method further comprises:
allowing a user to select a cardiac therapy scenario of a plurality of different cardiac therapy scenarios; and
displaying, on the graphical user interface, the plurality of electrode signals over a plurality of cardiac cycles corresponding to the selected cardiac therapy scenario.

Embodiment 15

The embodiment of embodiment 14, wherein each of the plurality of different cardiac therapy scenarios comprise at least one different pacing configuration, AV delay, and LV pacing site.

Embodiment 16

The embodiment as set forth in any one of embodiments 6-15, wherein the computing apparatus is further configured to execute or the method further comprises selecting one cardiac cycle of the plurality of cardiac cycles comprises selecting the cardiac cycle of the plurality of cardiac based on at least one metric for each cardiac cycle based on a single-cycle submetric and a cycle-series submetric, wherein the single-cycle submetric is based on at least two of the plurality of electrical signals during the cardiac cycle and the cycle-series submetric is based on at least two of the plurality of electrical signals during at least two cardiac cycles.

Embodiment 17

The embodiment as set forth in any one of embodiments 6-16, wherein the computing apparatus is further configured to execute or the method further comprises allowing a user to select an electrode set of a plurality of different electrode sets of the plurality of external electrodes, wherein the displayed plurality of electrode signals over the plurality of cardiac cycles comprises only electrode signals of the selected electrode set, and the displayed graphical map of electrical activation is based on the monitored electrical activity from only electrode signals of the selected electrode set.

Embodiment 18

A system for use in cardiac evaluation comprising:
electrode apparatus comprising a plurality of external electrodes to be located proximate a patient's skin;
display comprising a graphical user interface to present information for use in assisting a user in at least one of assessing a patient's cardiac health, evaluating and adjusting cardiac therapy delivered to a patient, and navigating at least one implantable electrode to a region of the patient's heart; and
computing apparatus comprising processing circuitry, the computing apparatus operably coupled to the electrode apparatus and the display, the computing apparatus configured to:
monitor electrical activity from the patient's skin using the plurality of external electrodes for each of a plurality of different cardiac therapy scenarios,
generate electrical heterogeneity information for each of the plurality of different cardiac therapy scenarios based on the monitored electrical activity,
display, on the graphical user interface, a cardiac therapy scenario selection region to allow a user to select one or more of the plurality of different cardiac therapy scenarios, and
displaying a ranking of the selected cardiac therapy scenarios based on the generated electrical heterogeneity information.

Embodiment 19

A method comprising:
providing a plurality of external electrodes to be located proximate a patient's skin;
monitoring electrical activity from the patient's skin using the plurality of external electrodes for each of a plurality of different cardiac therapy scenarios;

generating electrical heterogeneity information for each of the plurality of different cardiac therapy scenarios based on the monitored electrical activity;

displaying, on a graphical user interface, a cardiac therapy scenario selection region to allow a user to select one or more of the plurality of different cardiac therapy scenarios; and displaying a ranking of the selected cardiac therapy scenarios based on the generated electrical heterogeneity information.

Embodiment 20

The embodiment as set forth in any one of embodiments 18-19, wherein the electrical heterogeneity information comprises a global standard deviation of surrogate electrical activation times monitored by the plurality of external electrodes.

Embodiment 21

The embodiment as set forth in any one of embodiments 18-20, wherein the plurality of electrodes comprises two or more left external electrodes configured to be located proximate the left side of the patient, wherein the electrical heterogeneity information comprises an average of electrical activation times monitored by the two or more left external electrodes.

Embodiment 22

The embodiment as set forth in any one of embodiments 18-21, wherein the selected cardiac therapy scenarios are ranked based on a primary metric of electrical heterogeneity.

Embodiment 23

The embodiment as set forth in embodiment 22, wherein two or more of the selected cardiac therapy scenarios are further ranked based on a secondary metric of electrical heterogeneity if the primary metric of electrical heterogeneity of the two more selected cardiac therapy scenarios are within a selected threshold from each other.

Embodiment 24

The embodiment as set forth in any one of embodiments 18-24, wherein displaying a ranking of the selected cardiac therapy scenarios based on the generated cardiac heterogeneity information comprises displaying a plurality of rankings of the different groups of selected cardiac therapy scenarios.

Embodiment 25

A system for use in cardiac evaluation comprising:
electrode apparatus comprising a plurality of external electrodes to be located proximate a patient's skin;
display comprising a graphical user interface to present information for use in assisting a user in at least one of assessing a patient's cardiac health, evaluating and adjusting cardiac therapy delivered to a patient, and navigating at least one implantable electrode to a region of the patient's heart; and
computing apparatus comprising processing circuitry, the computing apparatus operably coupled to the electrode apparatus and the display, the computing apparatus configured to:

monitor electrical activity from the patient's skin using the plurality of external electrodes for each of a plurality of different cardiac therapy scenarios, and display, on the graphical user interface, a plurality of graphical maps of electrical activation based on the monitored electrical activity, each of the plurality of graphical maps of electrical activation corresponding to a different cardiac therapy scenario of the plurality of different cardiac therapy scenarios than each other.

Embodiment 26

A method comprising:
providing a plurality of external electrodes to be located proximate a patient's skin;
monitoring electrical activity from the patient's skin using the plurality of external electrodes for each of a plurality of different cardiac therapy scenarios, and
displaying, on a graphical user interface, a plurality of graphical maps of electrical activation based on the monitored electrical activity, each of the plurality of graphical maps of electrical activation corresponding to a different cardiac therapy scenario of the plurality of different cardiac therapy scenarios than each other.

Embodiment 27

The embodiment as set forth in any one of embodiments 25-26, wherein each of the plurality of different cardiac therapy scenarios comprise at least one different pacing configuration, AV delay, and LV pacing site.

Embodiment 28

The embodiment as set forth in any one of embodiments 25-27, wherein the computing apparatus is further configured to execute or the method further comprises:
generating electrical heterogeneity information for each of the plurality of different cardiac therapy scenarios based on the monitored electrical activity; and
displaying the electrical heterogeneity information proximate to each of the plurality of graphical maps of electrical activation corresponding to the same cardiac therapy scenario as the graphical map of electrical activation.

Embodiment 29

The embodiment as set forth in embodiment 28, wherein the plurality of electrodes comprises two or more left external electrodes configured to be located proximate the left side of the patient, wherein the electrical heterogeneity information comprises at least one of:
a global standard deviation of surrogate electrical activation times monitored by the plurality of external electrodes; and
a left metric of electrical activation times monitored by the two or more left external electrodes.

Embodiment 30

The embodiment as set forth in any one of embodiments 28-29, wherein the electrical heterogeneity information comprises a percentage change in the electrical heterogeneity information determined from electrical activity monitored during the corresponding cardiac therapy scenario and electrical heterogeneity information determined from electrical activity monitored during intrinsic cardiac activation.

Embodiment 31

The embodiment as set forth in any one of embodiments 25-30, wherein the computing apparatus is further configured to execute or the method further comprises displaying, on the graphical user interface, a graphical map of intrinsic electrical activation based on electrical activity monitored during intrinsic cardiac activation.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system for use in cardiac evaluation comprising:
electrode apparatus comprising a plurality of external electrodes to be located proximate a patient's skin;
display comprising a graphical user interface to present information for use in assisting a user in at least one of assessing a patient's cardiac health, evaluating and adjusting cardiac therapy delivered to a patient, and navigating at least one implantable electrode to a region of the patient's heart; and
computing apparatus comprising processing circuitry, the computing apparatus operably coupled to the electrode apparatus and the display, the computing apparatus configured to:
monitor electrical activity from the patient's skin using the plurality of external electrodes,
display, on the graphical user interface, a graphical map comprises a plurality of electrode graphical elements corresponding to and positioned on the graphical map in relation to the physical location of the plurality of electrodes located proximate the patient's skin, wherein the graphical map extends from a left portion corresponding to anterior side of the patient to a middle portion corresponding to the left side of the patient to a right side corresponding to the posterior side of the patient, and
display, on the graphical user interface, an effectiveness value proximate each of the plurality of electrode graphical elements representative of the effectiveness of the corresponding electrode in providing a valid sensing signal from the tissue of the patient.

2. The system of claim 1, wherein the computing apparatus is further configured to display, on the graphical user interface, a principal electrodes graphical region proximate one or more electrode graphical elements to indicate which of the plurality of electrodes most significant.

3. The system of claim 1, wherein the effectiveness value comprises one of the following three values: good signal, poor signal, and not in contact.

4. The system of claim 1, wherein the computing apparatus is further configured to display, on the graphical user interface, a global electrode connection status message indicative of the state of the plurality of electrodes providing valid sensing signals from the tissue of the patient.

5. A method comprising:
providing a plurality of external electrodes to be located proximate a patient's skin;
monitoring electrical activity from the patient's skin using the plurality of external electrodes;
displaying, on the graphical user interface, a graphical map comprising a plurality of electrode graphical elements corresponding to and positioned on the graphical map in relation to the physical location of the plurality of electrodes located proximate the patient's skin, wherein the graphical map extends from a left portion corresponding to anterior side of the patient to a middle portion corresponding to the left side of the patient to a right side corresponding to the posterior side of the patient; and
displaying, on the graphical user interface, an effectiveness value proximate each of the plurality of electrode graphical elements representative of the effectiveness of the corresponding electrode in providing a valid sensing signal from the tissue of the patient.

6. The method of claim 5, further comprising displaying, on the graphical user interface, a principal electrodes graphical region proximate one or more electrode graphical elements to indicate which of the plurality of electrodes most significant.

7. The method of claim 5, wherein the effectiveness value comprises one of the following three values: good signal, poor signal, and not in contact.

8. The method of claim 5, further comprising displaying, on the graphical user interface, a global electrode connection status message indicative of the state of the plurality of electrodes providing valid sensing signals from the tissue of the patient.

9. A system for use in cardiac evaluation comprising:
electrode apparatus comprising a plurality of external electrodes to be located proximate a patient's skin;
display comprising a graphical user interface to present information for use in assisting a user in at least one of assessing a patient's cardiac health, evaluating and adjusting cardiac therapy delivered to a patient, and navigating at least one implantable electrode to a region of the patient's heart; and
computing apparatus comprising processing circuitry, the computing apparatus operably coupled to the electrode apparatus and the display, the computing apparatus configured to:
monitor electrical activity from the patient's skin using the plurality of external electrodes resulting in a plurality of electrode signals,
display, on the graphical user interface, the plurality of electrode signals over a plurality of cardiac cycles,
select or allow a user to select one cardiac cycle of the plurality of cardiac cycles, and
display, on the graphical user interface, a graphical map of electrical activation based on the monitored electrical activity for the selected cardiac cycle.

10. The system of claim 9, wherein the computing apparatus is further configured to display, on the graphical user interface, a plurality of electrode elements corresponding to and positioned on the graphical map of electrical activation in relation to the physical location of the plurality of electrodes located proximate the patient's skin, wherein the graphical map extends from a left portion corresponding to anterior side of the patient to a middle portion corresponding to the left side of the patient to a right side corresponding to the posterior side of the patient.

11. The system of claim 10, wherein the computing apparatus is further configured to allow a user to hide or display the plurality of electrode elements.

12. The system of claim 10, wherein the computing apparatus is further configured to graphically indicate, on the graphical map of electrical activation, one or more areas of cardiac conduction block based on the monitored electrical activity for the selected cardiac cycle.

13. The system of claim 10, wherein the computing apparatus is further configured to graphically indicate, on the graphical user interface, which of the plurality of electrode elements corresponds to electrodes that are ineffective in providing a valid sensing signal from the tissue of the patient.

14. The system of claim 9, wherein the computing apparatus is further configured to interpolate the electrical activation of each area of the graphical map of electrical activation corresponding corresponds to external electrodes that are ineffective in providing a valid sensing signal from the tissue of the patient.

15. The system of claim 9, wherein the computing apparatus is further configured to display at least one metric of electrical heterogeneity based on the monitored electrical activity for the selected cardiac cycle.

16. The system of claim 9, wherein the computing apparatus is further configured to:
allow a user to select a cardiac therapy scenario of a plurality of different cardiac therapy scenarios; and
display, on the graphical user interface, the plurality of electrode signals over a plurality of cardiac cycles corresponding to the selected cardiac therapy scenario.

17. The system of claim 16, wherein each of the plurality of different cardiac therapy scenarios comprise at least one different pacing configuration, AV delay, and LV pacing site.

18. The system of claim 9, wherein the computing apparatus is further configured to allow a user to select an electrode set of a plurality of different electrode sets of the plurality of external electrodes,
wherein the displayed plurality of electrode signals over the plurality of cardiac cycles comprises only electrode signals of the selected electrode set, and the displayed graphical map of electrical activation is based on the monitored electrical activity from only electrode signals of the selected electrode set.

19. A method comprising:
providing a plurality of external electrodes to be located proximate a patient's skin;
monitoring electrical activity from the patient's skin using the plurality of external electrodes resulting in a plurality of electrode signals;
displaying, on the graphical user interface, the plurality of electrode signals over a plurality of cardiac cycles;
selecting or allowing a user to select one cardiac cycle of the plurality of cardiac cycles; and
displaying, on the graphical user interface, a graphical map of electrical activation based on the monitored electrical activity for the selected cardiac cycle.

20. The method of claim 19, the method further comprising displaying, on the graphical user interface, a plurality of electrode elements corresponding to and positioned on the graphical map of electrical activation in relation to the physical location of the plurality of electrodes located proximate the patient's skin, wherein the graphical map extends from a left portion corresponding to anterior side of the patient to a middle portion corresponding to the left side of the patient to a right side corresponding to the posterior side of the patient.

21. The method of claim 20, the method further comprising allowing a user to hide or display the plurality of electrode elements.

22. The method of claim 20, the method further comprising graphically indicating, on the graphical map of electrical activation, one or more areas of cardiac conduction block based on the monitored electrical activity for the selected cardiac cycle.

23. The method of claim 20, the method further comprising graphically indicating, on the graphical user interface, which of the plurality of electrode elements corresponds to electrodes that are ineffective in providing a valid sensing signal from the tissue of the patient.

24. The method of claim 19, the method further comprising interpolating the electrical activation of each area of the graphical map of electrical activation corresponding corresponds to external electrodes that are ineffective in providing a valid sensing signal from the tissue of the patient.

25. The method of claim 19, the method further comprising displaying at least one metric of electrical heterogeneity based on the monitored electrical activity for the selected cardiac cycle.

26. The method of claim 19, the method further comprising:
allowing a user to select a cardiac therapy scenario of a plurality of different cardiac therapy scenarios; and
displaying, on the graphical user interface, the plurality of electrode signals over a plurality of cardiac cycles corresponding to the selected cardiac therapy scenario.

27. The method of claim 26, wherein each of the plurality of different cardiac therapy scenarios comprise at least one different pacing configuration, AV delay, and LV pacing site.

28. The method of claim 19, the method further comprising allowing a user to select an electrode set of a plurality of different electrode sets of the plurality of external electrodes,
wherein the displayed plurality of electrode signals over the plurality of cardiac cycles comprises only electrode signals of the selected electrode set, and the displayed graphical map of electrical activation is based on the monitored electrical activity from only electrode signals of the selected electrode set.

* * * * *